United States Patent
Kakeshita et al.

(10) Patent No.: US 11,261,436 B2
(45) Date of Patent: Mar. 1, 2022

(54) MUTANT β-GLUCOSIDASE

(71) Applicant: Kao Corporation, Tokyo (JP)

(72) Inventors: Hiroshi Kakeshita, Wakayama (JP);
Nozomu Shibata, Wakayama (JP);
Junichi Sumitani, Sakai (JP); Yutaro Baba, Toyama (JP); Shuji Tani, Sakai (JP); Takashi Kawaguchi, Minoh (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 16/971,341

(22) PCT Filed: Feb. 21, 2019

(86) PCT No.: PCT/JP2019/006542
§ 371 (c)(1),
(2) Date: Aug. 20, 2020

(87) PCT Pub. No.: WO2019/163886
PCT Pub. Date: Aug. 29, 2019

(65) Prior Publication Data
US 2021/0017511 A1  Jan. 21, 2021

(30) Foreign Application Priority Data
Feb. 26, 2018  (JP) .............................. JP2018-031809

(51) Int. Cl.
C12N 9/42 (2006.01)
C12N 1/14 (2006.01)
(Continued)

(52) U.S. Cl.
CPC ............ *C12N 9/2445* (2013.01); *C12N 1/14* (2013.01); *C12N 15/52* (2013.01); *C12N 15/80* (2013.01);
(Continued)

(58) Field of Classification Search
None
See application file for complete search history.

(56) References Cited

U.S. PATENT DOCUMENTS

2010/0041104 A1  2/2010  Cascao-Pereira et al.
2010/0221778 A1  9/2010  Scott et al.
(Continued)

FOREIGN PATENT DOCUMENTS

JP  2011-523854 A  8/2011
JP  2011-223962 A  11/2011
(Continued)

OTHER PUBLICATIONS

GenBank Accession No. RAL09885.1, published Jun. 22, 2018 (Year: 2018).*

(Continued)

*Primary Examiner* — Richard C Ekstrom
(74) *Attorney, Agent, or Firm* — Sterne, Kessler, Goldstein & Fox P.L.L.C.

(57) ABSTRACT

Provided is a mutant β-glucosidase capable of more efficiently saccharifying biomass. A mutant β-glucosidase comprising an amino acid sequence having at least 80% sequence identity to SEQ ID NO: 1, wherein the amino acid sequence has asparagine at one or more positions selected from the group consisting of positions corresponding to positions 787, 790, and 797 of SEQ ID NO: 1, and has β-glucosidase activity.

24 Claims, 1 Drawing Sheet

Specification includes a Sequence Listing.

(51) Int. Cl.
*C12N 15/52* (2006.01)
*C12N 15/80* (2006.01)
*C12P 19/02* (2006.01)
*C12P 19/14* (2006.01)

(52) U.S. Cl.
CPC ............... *C12P 19/02* (2013.01); *C12P 19/14* (2013.01); *C12Y 302/01021* (2013.01)

(56) References Cited

U.S. PATENT DOCUMENTS

| | | |
|---|---|---|
| 2013/0143301 A1 | 6/2013 | Bott et al. |
| 2014/0127759 A1 | 5/2014 | Kurihara et al. |
| 2014/0186897 A1 | 7/2014 | Okada et al. |
| 2021/0017511 A1* | 1/2021 | Kakeshita ............... C12P 21/02 |

FOREIGN PATENT DOCUMENTS

| | | |
|---|---|---|
| JP | 2015-211678 A | 11/2015 |
| JP | 2016-015894 A | 2/2016 |
| WO | WO 2009/149202 A2 | 12/2009 |
| WO | WO 2010/012102 A1 | 2/2010 |
| WO | WO 2010/096931 A1 | 9/2010 |
| WO | WO 2011/097713 A1 | 8/2011 |
| WO | WO 2012/128260 A1 | 9/2012 |
| WO | WO 2013/008480 A1 | 1/2013 |
| WO | WO 2013/115305 A1 | 8/2013 |

OTHER PUBLICATIONS

International Search Report for PCT/JP2019/006542; I.A. fd Feb. 21, 2019, dated May 21, 2019 from the Japan Patent Office, Tokyo, Japan.

International Preliminary Report on Patentability (IPRP), Chapter I of the Patent Cooperation Treaty, including the Written Opinion, for PCT/JP2019/006542; I.A. fd Feb. 21, 2019, dated Aug. 27, 2020, by the International Bureau of WIPO, Geneva, Switzerland.

Morikawa, Y, "Research Frontier of Biomass Degrading Enzymes—Focused on Cellulases and Hemicellulases," A. Kondo et al., editors, 2012, CMC Publishing Co,. Ltd., Japan, pp. 10-19.

Lima, MA et al., "*Aspergillus niger* β-glucosidase has a cellulase-like tadpole molecular shape: insights into glycoside hydrolase family 3 (GH3) β-glucosidase structure and function," J Biol Chem. Nov. 15, 2013;288(46):32991-3005. doi: 10.1074/jbc.M113.479279. Epub Sep. 24, 2013. PMID: 24064212; PMCID: PMC3 829149.

Zhu, Z et al., "Direct quantitative determination of adsorbed cellulase on lignocellulosic biomass with its application to study cellulase desorption for potential recycling," Analyst. Nov. 2009;134(11):2267-72. doi: 10.1039/b906065k. Epub Sep. 1, 2009. PMID: 19838414.

Tu, M et al., "Evaluating the distribution of cellulases and the recycling of free cellulases during the hydrolysis of lignocellulosic substrates," Biotechnol Prog. Mar.-Apr. 2007;23(2):398-406. doi: 10.1021/bp060354f. Epub Mar. 23, 2007. PMID: 17378581.

* cited by examiner

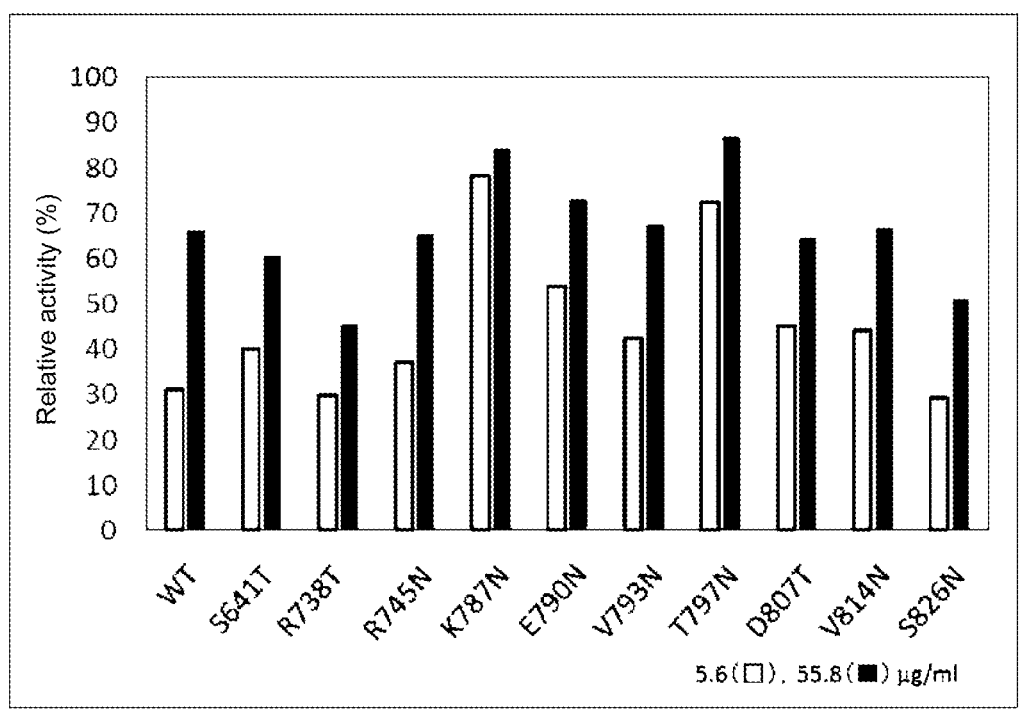

SEQUENCE LISTING

<160> NUMBER OF SEQ ID NOS: 19

<210> SEQ ID NO 1
<211> LENGTH: 841
<212> TYPE: PRT
<213> ORGANISM: Aspergillus aculeatus

<400> SEQUENCE: 1

Asp Glu Leu Ala Phe Ser Pro Pro Phe Tyr Pro Ser Pro Trp Ala Asn
1               5                   10                  15

Gly Gln Gly Glu Trp Ala Glu Ala Tyr Gln Arg Ala Val Ala Ile Val
            20                  25                  30

-continued

```
Ser Gln Met Thr Leu Asp Glu Lys Val Asn Leu Thr Thr Gly Thr Gly
         35                  40                  45
Trp Glu Leu Glu Lys Cys Val Gly Gln Thr Gly Gly Val Pro Arg Leu
 50                  55                  60
Asn Ile Gly Gly Met Cys Leu Gln Asp Ser Pro Leu Gly Ile Arg Asp
 65                  70                  75                  80
Ser Asp Tyr Asn Ser Ala Phe Pro Ala Gly Val Asn Val Ala Ala Thr
                 85                  90                  95
Trp Asp Lys Asn Leu Ala Tyr Leu Arg Gly Gln Ala Met Gly Gln Glu
                100                 105                 110
Phe Ser Asp Lys Gly Ile Asp Val Gln Leu Gly Pro Ala Ala Gly Pro
            115                 120                 125
Leu Gly Arg Ser Pro Asp Gly Gly Arg Asn Trp Glu Gly Phe Ser Pro
130                 135                 140
Asp Pro Ala Leu Thr Gly Val Leu Phe Ala Glu Thr Ile Lys Gly Ile
145                 150                 155                 160
Gln Asp Ala Gly Val Val Ala Thr Ala Lys His Tyr Ile Leu Asn Glu
                165                 170                 175
Gln Glu His Phe Arg Gln Val Ala Glu Ala Ala Gly Tyr Gly Phe Asn
            180                 185                 190
Ile Ser Asp Thr Ile Ser Ser Asn Val Asp Asp Lys Thr Ile His Glu
            195                 200                 205
Met Tyr Leu Trp Pro Phe Ala Asp Ala Val Arg Ala Gly Val Gly Ala
        210                 215                 220
Ile Met Cys Ser Tyr Asn Gln Ile Asn Asn Ser Tyr Gly Cys Gln Asn
225                 230                 235                 240
Ser Tyr Thr Leu Asn Lys Leu Leu Lys Ala Glu Leu Gly Phe Gln Gly
                245                 250                 255
Phe Val Met Ser Asp Trp Gly Ala His His Ser Gly Val Gly Ser Ala
            260                 265                 270
Leu Ala Gly Leu Asp Met Ser Met Pro Gly Asp Ile Thr Phe Asp Ser
        275                 280                 285
Ala Thr Ser Phe Trp Gly Thr Asn Leu Thr Ile Ala Val Leu Asn Gly
        290                 295                 300
Thr Val Pro Gln Trp Arg Val Asp Asp Met Ala Val Arg Ile Met Ala
305                 310                 315                 320
Ala Tyr Tyr Lys Val Gly Arg Asp Arg Leu Tyr Gln Pro Pro Asn Phe
                325                 330                 335
Ser Ser Trp Thr Arg Asp Glu Tyr Gly Phe Lys Tyr Phe Tyr Pro Gln
            340                 345                 350
Glu Gly Pro Tyr Glu Lys Val Asn His Phe Val Asn Val Gln Arg Asn
            355                 360                 365
His Ser Glu Val Ile Arg Lys Leu Gly Ala Asp Ser Thr Val Leu Leu
        370                 375                 380
Lys Asn Asn Asn Ala Leu Pro Leu Thr Gly Lys Glu Arg Lys Val Ala
385                 390                 395                 400
Ile Leu Gly Glu Asp Ala Gly Ser Asn Ser Tyr Gly Ala Asn Gly Cys
                405                 410                 415
Ser Asp Arg Gly Cys Asp Asn Gly Thr Leu Ala Met Ala Trp Gly Ser
            420                 425                 430
Gly Thr Ala Glu Phe Pro Tyr Leu Val Thr Pro Glu Gln Ala Ile Gln
        435                 440                 445
```

```
Ala Glu Val Leu Lys His Lys Gly Ser Val Tyr Ala Ile Thr Asp Asn
    450                 455                 460
Trp Ala Leu Ser Gln Val Glu Thr Leu Ala Lys Gln Ala Ser Val Ser
465                 470                 475                 480
Leu Val Phe Val Asn Ser Asp Ala Gly Glu Gly Tyr Ile Ser Val Asp
                485                 490                 495
Gly Asn Glu Gly Asp Arg Asn Asn Leu Thr Leu Trp Lys Asn Gly Asp
            500                 505                 510
Asn Leu Ile Lys Ala Ala Ala Asn Asn Cys Asn Asn Thr Ile Val Val
                515                 520                 525
Ile His Ser Val Gly Pro Val Leu Val Asp Glu Trp Tyr Asp His Pro
        530                 535                 540
Asn Val Thr Ala Ile Leu Trp Ala Gly Leu Pro Gly Gln Glu Ser Gly
545                 550                 555                 560
Asn Ser Leu Ala Asp Val Leu Tyr Gly Arg Val Asn Pro Gly Ala Lys
                565                 570                 575
Ser Pro Phe Thr Trp Gly Lys Thr Arg Glu Ala Tyr Gly Asp Tyr Leu
            580                 585                 590
Val Arg Glu Leu Asn Asn Gly Asn Gly Ala Pro Gln Asp Asp Phe Ser
        595                 600                 605
Glu Gly Val Phe Ile Asp Tyr Arg Gly Phe Asp Lys Arg Asn Glu Thr
610                 615                 620
Pro Ile Tyr Glu Phe Gly His Gly Leu Ser Tyr Thr Thr Phe Asn Tyr
625                 630                 635                 640
Ser Gly Leu His Ile Gln Val Leu Asn Ala Ser Ser Asn Ala Gln Val
                645                 650                 655
Ala Thr Glu Thr Gly Ala Ala Pro Thr Phe Gly Gln Val Gly Asn Ala
            660                 665                 670
Ser Asp Tyr Val Tyr Pro Glu Gly Leu Thr Arg Ile Ser Lys Phe Ile
        675                 680                 685
Tyr Pro Trp Leu Asn Ser Thr Asp Leu Lys Ala Ser Ser Gly Asp Pro
690                 695                 700
Tyr Tyr Gly Val Asp Thr Ala Glu His Val Pro Glu Gly Ala Thr Asp
705                 710                 715                 720
Gly Ser Pro Gln Pro Val Leu Pro Ala Gly Gly Ser Gly Gly Asn
                725                 730                 735
Pro Arg Leu Tyr Asp Glu Leu Ile Arg Val Ser Val Thr Val Lys Asn
            740                 745                 750
Thr Gly Arg Val Ala Gly Asp Ala Val Pro Gln Leu Tyr Val Ser Leu
        755                 760                 765
Gly Gly Pro Asn Glu Pro Lys Val Val Leu Arg Lys Phe Asp Arg Leu
770                 775                 780
Thr Leu Lys Pro Ser Glu Glu Thr Val Trp Thr Thr Thr Leu Thr Arg
785                 790                 795                 800
Arg Asp Leu Ser Asn Trp Asp Val Ala Ala Gln Asp Trp Val Ile Thr
                805                 810                 815
Ser Tyr Pro Lys Lys Val His Val Gly Ser Ser Ser Arg Gln Leu Pro
            820                 825                 830
Leu His Ala Ala Leu Pro Lys Val Gln
        835                 840
```

```
<210> SEQ ID NO 2
<211> LENGTH: 841
<212> TYPE: PRT
<213> ORGANISM: Aspergillus niger

<400> SEQUENCE: 2
```

Asp Glu Leu Ala Tyr Ser Pro Pro Tyr Pro Ser Pro Trp Ala Asn
1               5                   10                  15

Gly Gln Gly Asp Trp Ala Glu Ala Tyr Gln Arg Ala Val Asp Ile Val
            20                  25                  30

Ser Gln Met Thr Leu Ala Glu Lys Val Asn Leu Thr Thr Gly Thr Gly
            35                  40                  45

Trp Glu Leu Glu Leu Cys Val Gly Gln Thr Gly Gly Val Pro Arg Leu
    50                  55                  60

Gly Ile Pro Gly Met Cys Ala Gln Asp Ser Pro Leu Gly Val Arg Asp
65                  70                  75                  80

Ser Asp Tyr Asn Ser Ala Phe Pro Ala Gly Val Asn Val Ala Ala Thr
                85                  90                  95

Trp Asp Lys Asn Leu Ala Tyr Leu Arg Gly Gln Ala Met Gly Gln Glu
            100                 105                 110

Phe Ser Asp Lys Gly Ala Asp Ile Gln Leu Gly Pro Ala Ala Gly Pro
            115                 120                 125

Leu Gly Arg Ser Pro Asp Gly Gly Arg Asn Trp Glu Gly Phe Ser Pro
    130                 135                 140

Asp Pro Ala Leu Ser Gly Val Leu Phe Ala Glu Thr Ile Lys Gly Ile
145                 150                 155                 160

Gln Asp Ala Gly Val Val Ala Thr Ala Lys His Tyr Ile Ala Tyr Glu
                165                 170                 175

Gln Glu His Phe Arg Gln Ala Pro Glu Ala Gln Gly Tyr Gly Phe Asn
            180                 185                 190

Ile Thr Glu Ser Gly Ser Ala Asn Leu Asp Asp Lys Thr Met His Glu
            195                 200                 205

Leu Tyr Leu Trp Pro Phe Ala Asp Ala Ile Arg Ala Gly Ala Gly Ala
    210                 215                 220

Val Met Cys Ser Tyr Asn Gln Ile Asn Asn Ser Tyr Gly Cys Gln Asn
225                 230                 235                 240

Ser Tyr Thr Leu Asn Lys Leu Leu Lys Ala Glu Leu Gly Phe Gln Gly
                245                 250                 255

Phe Val Met Ser Asp Trp Ala Ala His His Ala Gly Val Ser Gly Ala
            260                 265                 270

Leu Ala Gly Leu Asp Met Ser Met Pro Gly Asp Val Asp Tyr Asp Ser
            275                 280                 285

Gly Thr Ser Tyr Trp Gly Thr Asn Leu Thr Ile Ser Val Leu Asn Gly
    290                 295                 300

Thr Val Pro Gln Trp Arg Val Asp Asp Met Ala Val Arg Ile Met Ala
305                 310                 315                 320

Ala Tyr Tyr Lys Val Gly Arg Asp Arg Leu Trp Thr Pro Pro Asn Phe
                325                 330                 335

Ser Ser Trp Thr Arg Asp Glu Tyr Gly Phe Lys Tyr Tyr Val Ser
            340                 345                 350

Glu Gly Pro Tyr Glu Lys Val Asn Gln Phe Val Asn Val Gln Arg Asn
            355                 360                 365

His Ser Glu Leu Ile Arg Arg Ile Gly Ala Asp Ser Thr Val Leu Leu
    370                 375                 380

```
Lys Asn Asp Gly Ala Leu Pro Leu Thr Gly Lys Glu Arg Leu Val Ala
385                 390                 395                 400

Leu Ile Gly Glu Asp Ala Gly Ser Asn Pro Tyr Gly Ala Asn Gly Cys
            405                 410                 415

Ser Asp Arg Gly Cys Asp Asn Gly Thr Leu Ala Met Gly Trp Gly Ser
        420                 425                 430

Gly Thr Ala Asn Phe Pro Tyr Leu Val Thr Pro Glu Gln Ala Ile Ser
            435                 440                 445

Asn Glu Val Leu Lys Asn Lys Asn Gly Val Phe Thr Ala Thr Asp Asn
    450                 455                 460

Trp Ala Ile Asp Gln Ile Glu Ala Leu Ala Lys Thr Ala Ser Val Ser
465                 470                 475                 480

Leu Val Phe Val Asn Ala Asp Ser Gly Glu Gly Tyr Ile Asn Val Asp
                485                 490                 495

Gly Asn Leu Gly Asp Arg Arg Asn Leu Thr Leu Trp Arg Asn Gly Asp
            500                 505                 510

Asn Val Ile Lys Ala Ala Ser Asn Cys Asn Asn Thr Ile Val Ile
                515                 520                 525

Ile His Ser Val Gly Pro Val Leu Val Asn Glu Trp Tyr Asp Asn Pro
530                 535                 540

Asn Val Thr Ala Ile Leu Trp Gly Gly Leu Pro Gly Gln Glu Ser Gly
545                 550                 555                 560

Asn Ser Leu Ala Asp Val Leu Tyr Gly Arg Val Asn Pro Gly Ala Lys
            565                 570                 575

Ser Pro Phe Thr Trp Gly Lys Thr Arg Glu Ala Tyr Gln Asp Tyr Leu
        580                 585                 590

Tyr Thr Glu Pro Asn Asn Gly Asn Gly Ala Pro Gln Glu Asp Phe Val
            595                 600                 605

Glu Gly Val Phe Ile Asp Tyr Arg Gly Phe Asp Lys Arg Asn Glu Thr
        610                 615                 620

Pro Ile Tyr Glu Phe Gly Tyr Gly Leu Ser Tyr Thr Thr Phe Asn Tyr
625                 630                 635                 640

Ser Asn Leu Gln Val Glu Val Leu Ser Ala Pro Ala Tyr Glu Pro Ala
            645                 650                 655

Ser Gly Glu Thr Glu Ala Ala Pro Thr Phe Gly Glu Val Gly Asn Ala
        660                 665                 670

Ser Asp Tyr Leu Tyr Pro Asp Gly Leu Gln Arg Ile Thr Lys Phe Ile
            675                 680                 685

Tyr Pro Trp Leu Asn Ser Thr Asp Leu Glu Ala Ser Ser Gly Asp Ala
690                 695                 700

Ser Tyr Gly Gln Asp Ala Ser Asp Tyr Leu Pro Glu Gly Ala Thr Asp
705                 710                 715                 720

Gly Ser Ala Gln Pro Ile Leu Pro Ala Gly Gly Ala Gly Gly Asn
            725                 730                 735

Pro Arg Leu Tyr Asp Glu Leu Ile Arg Val Ser Val Thr Ile Lys Asn
                740                 745                 750

Thr Gly Lys Val Ala Gly Asp Glu Val Pro Gln Leu Tyr Val Ser Leu
            755                 760                 765

Gly Gly Pro Asn Glu Pro Lys Ile Val Leu Arg Gln Phe Glu Arg Ile
    770                 775                 780

Thr Leu Gln Pro Ser Lys Glu Thr Gln Trp Ser Thr Thr Leu Thr Arg
785                 790                 795                 800
```

```
Arg Asp Leu Ala Asn Trp Asn Val Glu Thr Gln Asp Trp Glu Ile Thr
                805                 810                 815

Ser Tyr Pro Lys Met Val Phe Ala Gly Ser Ser Arg Lys Leu Pro
            820                 825                 830

Leu Arg Ala Ser Leu Pro Thr Val His
        835                 840

<210> SEQ ID NO 3
<211> LENGTH: 841
<212> TYPE: PRT
<213> ORGANISM: Aspergillus kawachii

<400> SEQUENCE: 3

Asp Glu Leu Ala Tyr Ser Pro Pro Tyr Tyr Pro Ser Pro Trp Ala Asn
1               5                   10                  15

Gly Gln Gly Asp Trp Ala Gln Ala Tyr Gln Arg Ala Val Asp Ile Val
            20                  25                  30

Ser Gln Met Thr Leu Ala Glu Lys Val Asn Leu Thr Thr Gly Thr Gly
        35                  40                  45

Trp Glu Leu Glu Leu Cys Val Gly Gln Thr Gly Gly Val Pro Arg Leu
50                  55                  60

Gly Val Pro Gly Met Cys Leu Gln Asp Ser Pro Leu Gly Val Arg Asp
65                  70                  75                  80

Ser Asp Tyr Asn Ser Ala Phe Pro Ser Gly Met Asn Val Ala Ala Thr
                85                  90                  95

Trp Asp Lys Asn Leu Ala Tyr Leu Arg Gly Lys Ala Met Gly Gln Glu
            100                 105                 110

Phe Ser Asp Lys Gly Ala Asp Ile Gln Leu Gly Pro Ala Ala Gly Pro
        115                 120                 125

Leu Gly Arg Ser Pro Asp Gly Gly Arg Asn Trp Glu Gly Phe Ser Pro
130                 135                 140

Asp Pro Ala Leu Ser Gly Val Leu Phe Ala Glu Thr Ile Lys Gly Ile
145                 150                 155                 160

Gln Asp Ala Gly Val Val Ala Thr Ala Lys His Tyr Ile Ala Tyr Glu
                165                 170                 175

Gln Glu His Phe Arg Gln Ala Pro Glu Ala Gln Gly Tyr Gly Phe Asn
            180                 185                 190

Ile Ser Glu Ser Gly Ser Ala Asn Leu Asp Asp Lys Thr Met His Glu
        195                 200                 205

Leu Tyr Leu Trp Pro Phe Ala Asp Ala Ile Arg Ala Gly Ala Gly Ala
210                 215                 220

Val Met Cys Ser Tyr Asn Gln Ile Asn Asn Ser Tyr Gly Cys Gln Asn
225                 230                 235                 240

Ser Tyr Thr Leu Asn Lys Leu Leu Lys Ala Glu Leu Gly Phe Gln Gly
                245                 250                 255

Phe Val Met Ser Asp Trp Ala Ala His His Ala Gly Val Ser Gly Ala
            260                 265                 270

Leu Ala Gly Leu Asp Met Ser Met Pro Gly Asp Val Asp Tyr Asp Ser
        275                 280                 285

Gly Thr Ser Tyr Trp Gly Thr Asn Leu Thr Val Ser Val Leu Asn Gly
290                 295                 300

Thr Val Pro Gln Trp Arg Val Asp Asp Met Ala Val Arg Ile Met Ala
305                 310                 315                 320

Ala Tyr Tyr Lys Val Gly Arg Asp Arg Leu Trp Thr Pro Pro Asn Phe
                325                 330                 335
```

```
Ser Ser Trp Thr Arg Asp Glu Tyr Gly Tyr Lys Tyr Tyr Val Ser
        340                 345                 350

Glu Gly Pro Tyr Glu Lys Val Asn His Tyr Val Asn Val Gln Arg Asn
            355                 360                 365

His Ser Glu Leu Ile Arg Arg Ile Gly Ala Asp Ser Thr Val Leu Leu
    370                 375                 380

Lys Asn Asp Gly Ala Leu Pro Leu Thr Gly Lys Glu Arg Leu Val Ala
385                 390                 395                 400

Leu Ile Gly Glu Asp Ala Gly Ser Asn Pro Tyr Gly Ala Asn Gly Cys
                405                 410                 415

Ser Asp Arg Gly Cys Asp Asn Gly Thr Leu Ala Met Gly Trp Gly Ser
            420                 425                 430

Gly Thr Ala Asn Phe Pro Tyr Leu Val Thr Pro Glu Gln Ala Ile Ser
        435                 440                 445

Asn Glu Val Leu Lys Asn Lys Asn Gly Val Phe Thr Ala Thr Asp Asn
    450                 455                 460

Trp Ala Ile Asp Gln Ile Glu Ala Leu Ala Lys Thr Ala Ser Val Ser
465                 470                 475                 480

Leu Val Phe Val Asn Ala Asp Ser Gly Glu Gly Tyr Ile Asn Val Asp
                485                 490                 495

Gly Asn Leu Gly Asp Arg Arg Asn Leu Thr Leu Trp Arg Asn Gly Asp
            500                 505                 510

Asn Val Ile Lys Ala Ala Ser Asn Cys Asn Asn Thr Ile Val Ile
        515                 520                 525

Ile His Ser Val Gly Pro Val Leu Val Asn Glu Trp Tyr Asp Asn Pro
    530                 535                 540

Asn Val Thr Ala Ile Leu Trp Gly Gly Leu Pro Gly Gln Glu Ser Gly
545                 550                 555                 560

Asn Ser Leu Ala Asp Val Leu Tyr Gly Arg Val Asn Pro Gly Ala Lys
                565                 570                 575

Ser Pro Phe Thr Trp Gly Lys Thr Arg Glu Ala Tyr Gln Asp Tyr Leu
            580                 585                 590

Val Thr Glu Pro Asn Asn Gly Asn Gly Ala Pro Gln Glu Asp Phe Val
        595                 600                 605

Glu Gly Val Phe Ile Asp Tyr Arg Gly Phe Asp Lys Arg Asn Glu Thr
    610                 615                 620

Pro Ile Tyr Glu Phe Gly Tyr Gly Leu Ser Tyr Thr Thr Phe Asn Tyr
625                 630                 635                 640

Ser Asn Leu Glu Val Gln Val Leu Ser Ala Pro Ala Tyr Glu Pro Ala
                645                 650                 655

Ser Gly Glu Thr Glu Ala Ala Pro Thr Phe Gly Glu Val Gly Asn Ala
            660                 665                 670

Ser Asn Tyr Leu Tyr Pro Asp Gly Leu Gln Lys Ile Thr Lys Phe Ile
        675                 680                 685

Tyr Pro Trp Leu Asn Ser Thr Asp Leu Glu Ala Ser Ser Gly Asp Ala
    690                 695                 700

Ser Tyr Gly Gln Asp Ser Ser Asp Tyr Leu Pro Glu Gly Ala Thr Asp
705                 710                 715                 720

Gly Ser Ala Gln Pro Ile Leu Pro Ala Gly Gly Pro Gly Gly Asn
                725                 730                 735

Pro Arg Leu Tyr Asp Glu Leu Ile Arg Val Ser Val Thr Ile Lys Asn
            740                 745                 750
```

```
Thr Gly Lys Val Ala Gly Asp Glu Val Pro Gln Leu Tyr Val Ser Leu
        755                 760                 765

Gly Gly Pro Asn Glu Pro Lys Ile Val Leu Arg Gln Phe Glu Arg Ile
770                 775                 780

Thr Leu Gln Pro Ser Glu Glu Thr Lys Trp Ser Thr Thr Leu Thr Arg
785                 790                 795                 800

Arg Asp Leu Ala Asn Trp Asn Val Glu Lys Gln Asp Trp Glu Ile Thr
                805                 810                 815

Ser Tyr Pro Lys Met Val Phe Val Gly Ser Ser Arg Lys Leu Pro
            820                 825                 830

Leu Arg Ala Ser Leu Pro Thr Val His
        835                 840

<210> SEQ ID NO 4
<211> LENGTH: 860
<212> TYPE: PRT
<213> ORGANISM: Aspergillus aculeatus

<400> SEQUENCE: 4

Met Lys Leu Ser Trp Leu Glu Ala Ala Leu Thr Ala Ala Ser Val
1               5                   10                  15

Val Ser Ala Asp Glu Leu Ala Phe Ser Pro Pro Phe Tyr Pro Ser Pro
                20                  25                  30

Trp Ala Asn Gly Gln Gly Glu Trp Ala Glu Ala Tyr Gln Arg Ala Val
            35                  40                  45

Ala Ile Val Ser Gln Met Thr Leu Asp Glu Lys Val Asn Leu Thr Thr
        50                  55                  60

Gly Thr Gly Trp Glu Leu Glu Lys Cys Val Gly Gln Thr Gly Gly Val
65                  70                  75                  80

Pro Arg Leu Asn Ile Gly Gly Met Cys Leu Gln Asp Ser Pro Leu Gly
                85                  90                  95

Ile Arg Asp Ser Asp Tyr Asn Ser Ala Phe Pro Ala Gly Val Asn Val
            100                 105                 110

Ala Ala Thr Trp Asp Lys Asn Leu Ala Tyr Leu Arg Gly Gln Ala Met
        115                 120                 125

Gly Gln Glu Phe Ser Asp Lys Gly Ile Asp Val Gln Leu Gly Pro Ala
130                 135                 140

Ala Gly Pro Leu Gly Arg Ser Pro Asp Gly Gly Arg Asn Trp Glu Gly
145                 150                 155                 160

Phe Ser Pro Asp Pro Ala Leu Thr Gly Val Leu Phe Ala Glu Thr Ile
                165                 170                 175

Lys Gly Ile Gln Asp Ala Gly Val Val Ala Thr Ala Lys His Tyr Ile
            180                 185                 190

Leu Asn Glu Gln Glu His Phe Arg Gln Val Ala Glu Ala Gly Tyr
        195                 200                 205

Gly Phe Asn Ile Ser Asp Thr Ile Ser Ser Asn Val Asp Asp Lys Thr
            210                 215                 220

Ile His Glu Met Tyr Leu Trp Pro Phe Ala Asp Ala Val Arg Ala Gly
225                 230                 235                 240

Val Gly Ala Ile Met Cys Ser Tyr Asn Gln Ile Asn Asn Ser Tyr Gly
                245                 250                 255

Cys Gln Asn Ser Tyr Thr Leu Asn Lys Leu Leu Lys Ala Glu Leu Gly
            260                 265                 270

Phe Gln Gly Phe Val Met Ser Asp Trp Gly Ala His His Ser Gly Val
        275                 280                 285
```

-continued

Gly Ser Ala Leu Ala Gly Leu Asp Met Ser Met Pro Gly Asp Ile Thr
290                 295                 300

Phe Asp Ser Ala Thr Ser Phe Trp Gly Thr Asn Leu Thr Ile Ala Val
305                 310                 315                 320

Leu Asn Gly Thr Val Pro Gln Trp Arg Val Asp Asp Met Ala Val Arg
            325                 330                 335

Ile Met Ala Ala Tyr Tyr Lys Val Gly Arg Asp Arg Leu Tyr Gln Pro
            340                 345                 350

Pro Asn Phe Ser Ser Trp Thr Arg Asp Glu Tyr Gly Phe Lys Tyr Phe
            355                 360                 365

Tyr Pro Gln Glu Gly Pro Tyr Glu Lys Val Asn His Phe Val Asn Val
370                 375                 380

Gln Arg Asn His Ser Glu Val Ile Arg Lys Leu Gly Ala Asp Ser Thr
385                 390                 395                 400

Val Leu Leu Lys Asn Asn Asn Ala Leu Pro Leu Thr Gly Lys Glu Arg
            405                 410                 415

Lys Val Ala Ile Leu Gly Glu Asp Ala Gly Ser Asn Ser Tyr Gly Ala
            420                 425                 430

Asn Gly Cys Ser Asp Arg Gly Cys Asp Asn Gly Thr Leu Ala Met Ala
            435                 440                 445

Trp Gly Ser Gly Thr Ala Glu Phe Pro Tyr Leu Val Thr Pro Glu Gln
450                 455                 460

Ala Ile Gln Ala Glu Val Leu Lys His Lys Gly Ser Val Tyr Ala Ile
465                 470                 475                 480

Thr Asp Asn Trp Ala Leu Ser Gln Val Glu Thr Leu Ala Lys Gln Ala
            485                 490                 495

Ser Val Ser Leu Val Phe Val Asn Ser Asp Ala Gly Glu Gly Tyr Ile
            500                 505                 510

Ser Val Asp Gly Asn Glu Gly Asp Arg Asn Asn Leu Thr Leu Trp Lys
            515                 520                 525

Asn Gly Asp Asn Leu Ile Lys Ala Ala Ala Asn Asn Cys Asn Asn Thr
530                 535                 540

Ile Val Val Ile His Ser Val Gly Pro Val Leu Val Asp Glu Trp Tyr
545                 550                 555                 560

Asp His Pro Asn Val Thr Ala Ile Leu Trp Ala Gly Leu Pro Gly Gln
            565                 570                 575

Glu Ser Gly Asn Ser Leu Ala Asp Val Leu Tyr Gly Arg Val Asn Pro
            580                 585                 590

Gly Ala Lys Ser Pro Phe Thr Trp Gly Lys Thr Arg Glu Ala Tyr Gly
            595                 600                 605

Asp Tyr Leu Val Arg Glu Leu Asn Asn Gly Asn Gly Ala Pro Gln Asp
            610                 615                 620

Asp Phe Ser Glu Gly Val Phe Ile Asp Tyr Arg Gly Phe Asp Lys Arg
625                 630                 635                 640

Asn Glu Thr Pro Ile Tyr Glu Phe Gly His Gly Leu Ser Tyr Thr Thr
            645                 650                 655

Phe Asn Tyr Ser Gly Leu His Ile Gln Val Leu Asn Ala Ser Ser Asn
            660                 665                 670

Ala Gln Val Ala Thr Glu Thr Gly Ala Ala Pro Thr Phe Gly Gln Val
            675                 680                 685

Gly Asn Ala Ser Asp Tyr Val Tyr Pro Glu Gly Leu Thr Arg Ile Ser
690                 695                 700

```
Lys Phe Ile Tyr Pro Trp Leu Asn Ser Thr Asp Leu Lys Ala Ser Ser
705                 710                 715                 720

Gly Asp Pro Tyr Tyr Gly Val Asp Thr Ala Glu His Val Pro Glu Gly
            725                 730                 735

Ala Thr Asp Gly Ser Pro Gln Pro Val Leu Pro Ala Gly Gly Gly Ser
            740                 745                 750

Gly Gly Asn Pro Arg Leu Tyr Asp Glu Leu Ile Arg Val Ser Val Thr
            755                 760                 765

Val Lys Asn Thr Gly Arg Val Ala Gly Asp Ala Val Pro Gln Leu Tyr
770                 775                 780

Val Ser Leu Gly Gly Pro Asn Glu Pro Lys Val Val Leu Arg Lys Phe
785                 790                 795                 800

Asp Arg Leu Thr Leu Lys Pro Ser Glu Thr Val Trp Thr Thr Thr
                805                 810                 815

Leu Thr Arg Arg Asp Leu Ser Asn Trp Asp Val Ala Ala Gln Asp Trp
            820                 825                 830

Val Ile Thr Ser Tyr Pro Lys Lys Val His Val Gly Ser Ser Ser Arg
            835                 840                 845

Gln Leu Pro Leu His Ala Ala Leu Pro Lys Val Gln
    850                 855                 860

<210> SEQ ID NO 5
<211> LENGTH: 860
<212> TYPE: PRT
<213> ORGANISM: Aspergillus niger

<400> SEQUENCE: 5

Met Arg Phe Thr Ser Ile Glu Ala Val Ala Leu Thr Ala Val Ser Leu
1               5                   10                  15

Ala Ser Ala Asp Glu Leu Ala Tyr Ser Pro Pro Tyr Tyr Pro Ser Pro
            20                  25                  30

Trp Ala Asn Gly Gln Gly Asp Trp Ala Glu Ala Tyr Gln Arg Ala Val
        35                  40                  45

Asp Ile Val Ser Gln Met Thr Leu Ala Glu Lys Val Asn Leu Thr Thr
50                  55                  60

Gly Thr Gly Trp Glu Leu Glu Leu Cys Val Gly Gln Thr Gly Gly Val
65                  70                  75                  80

Pro Arg Leu Gly Ile Pro Gly Met Cys Ala Gln Asp Ser Pro Leu Gly
                85                  90                  95

Val Arg Asp Ser Asp Tyr Asn Ser Ala Phe Pro Ala Gly Val Asn Val
            100                 105                 110

Ala Ala Thr Trp Asp Lys Asn Leu Ala Tyr Leu Arg Gly Gln Ala Met
        115                 120                 125

Gly Gln Glu Phe Ser Asp Lys Gly Ala Asp Ile Gln Leu Gly Pro Ala
    130                 135                 140

Ala Gly Pro Leu Gly Arg Ser Pro Asp Gly Gly Arg Asn Trp Glu Gly
145                 150                 155                 160

Phe Ser Pro Asp Pro Ala Leu Ser Gly Val Leu Phe Ala Glu Thr Ile
                165                 170                 175

Lys Gly Ile Gln Asp Ala Gly Val Val Ala Thr Ala Lys His Tyr Ile
            180                 185                 190

Ala Tyr Glu Gln Glu His Phe Arg Gln Ala Pro Glu Ala Gln Gly Tyr
        195                 200                 205

Gly Phe Asn Ile Thr Glu Ser Gly Ser Ala Asn Leu Asp Asp Lys Thr
    210                 215                 220
```

```
Met His Glu Leu Tyr Leu Trp Pro Phe Ala Asp Ala Ile Arg Ala Gly
225                 230                 235                 240

Ala Gly Ala Val Met Cys Ser Tyr Asn Gln Ile Asn Asn Ser Tyr Gly
            245                 250                 255

Cys Gln Asn Ser Tyr Thr Leu Asn Lys Leu Leu Lys Ala Glu Leu Gly
        260                 265                 270

Phe Gln Gly Phe Val Met Ser Asp Trp Ala Ala His His Ala Gly Val
    275                 280                 285

Ser Gly Ala Leu Ala Gly Leu Asp Met Ser Met Pro Gly Asp Val Asp
290                 295                 300

Tyr Asp Ser Gly Thr Ser Tyr Trp Gly Thr Asn Leu Thr Ile Ser Val
305                 310                 315                 320

Leu Asn Gly Thr Val Pro Gln Trp Arg Val Asp Asp Met Ala Val Arg
            325                 330                 335

Ile Met Ala Ala Tyr Tyr Lys Val Gly Arg Asp Arg Leu Trp Thr Pro
        340                 345                 350

Pro Asn Phe Ser Ser Trp Thr Arg Asp Glu Tyr Gly Phe Lys Tyr Tyr
    355                 360                 365

Tyr Val Ser Glu Gly Pro Tyr Glu Lys Val Asn Gln Phe Val Asn Val
370                 375                 380

Gln Arg Asn His Ser Glu Leu Ile Arg Arg Ile Gly Ala Asp Ser Thr
385                 390                 395                 400

Val Leu Leu Lys Asn Asp Gly Ala Leu Pro Leu Thr Gly Lys Glu Arg
            405                 410                 415

Leu Val Ala Leu Ile Gly Glu Asp Ala Gly Ser Asn Pro Tyr Gly Ala
        420                 425                 430

Asn Gly Cys Ser Asp Arg Gly Cys Asp Asn Gly Thr Leu Ala Met Gly
    435                 440                 445

Trp Gly Ser Gly Thr Ala Asn Phe Pro Tyr Leu Val Thr Pro Glu Gln
450                 455                 460

Ala Ile Ser Asn Glu Val Leu Lys Asn Lys Asn Gly Val Phe Thr Ala
465                 470                 475                 480

Thr Asp Asn Trp Ala Ile Asp Gln Ile Glu Ala Leu Ala Lys Thr Ala
            485                 490                 495

Ser Val Ser Leu Val Phe Val Asn Ala Asp Ser Gly Glu Gly Tyr Ile
        500                 505                 510

Asn Val Asp Gly Asn Leu Gly Asp Arg Arg Asn Leu Thr Leu Trp Arg
    515                 520                 525

Asn Gly Asp Asn Val Ile Lys Ala Ala Ala Ser Asn Cys Asn Asn Thr
530                 535                 540

Ile Val Ile Ile His Ser Val Gly Pro Val Leu Val Asn Glu Trp Tyr
545                 550                 555                 560

Asp Asn Pro Asn Val Thr Ala Ile Leu Trp Gly Gly Leu Pro Gly Gln
            565                 570                 575

Glu Ser Gly Asn Ser Leu Ala Asp Val Leu Tyr Gly Arg Val Asn Pro
        580                 585                 590

Gly Ala Lys Ser Pro Phe Thr Trp Gly Lys Thr Arg Glu Ala Tyr Gln
    595                 600                 605

Asp Tyr Leu Tyr Thr Glu Pro Asn Asn Gly Asn Gly Ala Pro Gln Glu
610                 615                 620

Asp Phe Val Glu Gly Val Phe Ile Asp Tyr Arg Gly Phe Asp Lys Arg
625                 630                 635                 640
```

-continued

```
Asn Glu Thr Pro Ile Tyr Glu Phe Gly Tyr Gly Leu Ser Tyr Thr Thr
                645                 650                 655

Phe Asn Tyr Ser Asn Leu Gln Val Glu Val Leu Ser Ala Pro Ala Tyr
            660                 665                 670

Glu Pro Ala Ser Gly Glu Thr Glu Ala Ala Pro Thr Phe Gly Glu Val
        675                 680                 685

Gly Asn Ala Ser Asp Tyr Leu Tyr Pro Asp Gly Leu Gln Arg Ile Thr
    690                 695                 700

Lys Phe Ile Tyr Pro Trp Leu Asn Ser Thr Asp Leu Glu Ala Ser Ser
705                 710                 715                 720

Gly Asp Ala Ser Tyr Gly Gln Asp Ala Ser Asp Tyr Leu Pro Glu Gly
                725                 730                 735

Ala Thr Asp Gly Ser Ala Gln Pro Ile Leu Pro Ala Gly Gly Gly Ala
            740                 745                 750

Gly Gly Asn Pro Arg Leu Tyr Asp Glu Leu Ile Arg Val Ser Val Thr
        755                 760                 765

Ile Lys Asn Thr Gly Lys Val Ala Gly Asp Glu Val Pro Gln Leu Tyr
    770                 775                 780

Val Ser Leu Gly Gly Pro Asn Glu Pro Lys Ile Val Leu Arg Gln Phe
785                 790                 795                 800

Glu Arg Ile Thr Leu Gln Pro Ser Lys Glu Thr Gln Trp Ser Thr Thr
                805                 810                 815

Leu Thr Arg Arg Asp Leu Ala Asn Trp Asn Val Glu Thr Gln Asp Trp
            820                 825                 830

Glu Ile Thr Ser Tyr Pro Lys Met Val Phe Ala Gly Ser Ser Ser Arg
        835                 840                 845

Lys Leu Pro Leu Arg Ala Ser Leu Pro Thr Val His
    850                 855                 860

<210> SEQ ID NO 6
<211> LENGTH: 860
<212> TYPE: PRT
<213> ORGANISM: Aspergillus kawachii

<400> SEQUENCE: 6

Met Arg Phe Thr Leu Ile Glu Ala Val Ala Leu Thr Ala Val Ser Leu
1               5                   10                  15

Ala Ser Ala Asp Glu Leu Ala Tyr Ser Pro Tyr Tyr Pro Ser Pro
            20                  25                  30

Trp Ala Asn Gly Gln Gly Asp Trp Ala Gln Ala Tyr Gln Arg Ala Val
        35                  40                  45

Asp Ile Val Ser Gln Met Thr Leu Ala Glu Lys Val Asn Leu Thr Thr
    50                  55                  60

Gly Thr Gly Trp Glu Leu Glu Leu Cys Val Gly Gln Thr Gly Gly Val
65                  70                  75                  80

Pro Arg Leu Gly Val Pro Gly Met Cys Leu Gln Asp Ser Pro Leu Gly
                85                  90                  95

Val Arg Asp Ser Asp Tyr Asn Ser Ala Phe Pro Ser Gly Met Asn Val
            100                 105                 110

Ala Ala Thr Trp Asp Lys Asn Leu Ala Tyr Leu Arg Gly Lys Ala Met
        115                 120                 125

Gly Gln Glu Phe Ser Asp Lys Gly Ala Asp Ile Gln Leu Gly Pro Ala
    130                 135                 140

Ala Gly Pro Leu Gly Arg Ser Pro Asp Gly Gly Arg Asn Trp Glu Gly
145                 150                 155                 160
```

```
Phe Ser Pro Asp Pro Ala Leu Ser Gly Val Leu Phe Ala Glu Thr Ile
            165                 170                 175

Lys Gly Ile Gln Asp Ala Gly Val Val Ala Thr Ala Lys His Tyr Ile
            180                 185                 190

Ala Tyr Glu Gln Glu His Phe Arg Gln Ala Pro Glu Ala Gln Gly Tyr
            195                 200                 205

Gly Phe Asn Ile Ser Glu Ser Gly Ser Ala Asn Leu Asp Asp Lys Thr
            210                 215                 220

Met His Glu Leu Tyr Leu Trp Pro Phe Ala Asp Ala Ile Arg Ala Gly
225                 230                 235                 240

Ala Gly Ala Val Met Cys Ser Tyr Asn Gln Ile Asn Asn Ser Tyr Gly
            245                 250                 255

Cys Gln Asn Ser Tyr Thr Leu Asn Lys Leu Leu Lys Ala Glu Leu Gly
            260                 265                 270

Phe Gln Gly Phe Val Met Ser Asp Trp Ala Ala His His Ala Gly Val
            275                 280                 285

Ser Gly Ala Leu Ala Gly Leu Asp Met Ser Met Pro Gly Asp Val Asp
            290                 295                 300

Tyr Asp Ser Gly Thr Ser Tyr Trp Gly Thr Asn Leu Thr Val Ser Val
305                 310                 315                 320

Leu Asn Gly Thr Val Pro Gln Trp Arg Val Asp Asp Met Ala Val Arg
            325                 330                 335

Ile Met Ala Ala Tyr Tyr Lys Val Gly Arg Asp Arg Leu Trp Thr Pro
            340                 345                 350

Pro Asn Phe Ser Ser Trp Thr Arg Asp Glu Tyr Gly Tyr Lys Tyr Tyr
            355                 360                 365

Tyr Val Ser Glu Gly Pro Tyr Glu Lys Val Asn His Tyr Val Asn Val
            370                 375                 380

Gln Arg Asn His Ser Glu Leu Ile Arg Arg Ile Gly Ala Asp Ser Thr
385                 390                 395                 400

Val Leu Leu Lys Asn Asp Gly Ala Leu Pro Leu Thr Gly Lys Glu Arg
            405                 410                 415

Leu Val Ala Leu Ile Gly Glu Asp Ala Gly Ser Asn Pro Tyr Gly Ala
            420                 425                 430

Asn Gly Cys Ser Asp Arg Gly Cys Asp Asn Gly Thr Leu Ala Met Gly
            435                 440                 445

Trp Gly Ser Gly Thr Ala Asn Phe Pro Tyr Leu Val Thr Pro Glu Gln
            450                 455                 460

Ala Ile Ser Asn Glu Val Leu Lys Asn Lys Asn Gly Val Phe Thr Ala
465                 470                 475                 480

Thr Asp Asn Trp Ala Ile Asp Gln Ile Glu Ala Leu Ala Lys Thr Ala
            485                 490                 495

Ser Val Ser Leu Val Phe Val Asn Ala Asp Ser Gly Glu Gly Tyr Ile
            500                 505                 510

Asn Val Asp Gly Asn Leu Gly Asp Arg Arg Asn Leu Thr Leu Trp Arg
            515                 520                 525

Asn Gly Asp Asn Val Ile Lys Ala Ala Ser Asn Cys Asn Asn Thr
            530                 535                 540

Ile Val Ile Ile His Ser Val Gly Pro Val Leu Val Asn Glu Trp Tyr
545                 550                 555                 560

Asp Asn Pro Asn Val Thr Ala Ile Leu Trp Gly Gly Leu Pro Gly Gln
            565                 570                 575
```

Glu Ser Gly Asn Ser Leu Ala Asp Val Leu Tyr Gly Arg Val Asn Pro
            580                 585                 590

Gly Ala Lys Ser Pro Phe Thr Trp Gly Lys Thr Arg Glu Ala Tyr Gln
        595                 600                 605

Asp Tyr Leu Val Thr Glu Pro Asn Asn Gly Asn Gly Ala Pro Gln Glu
    610                 615                 620

Asp Phe Val Glu Gly Val Phe Ile Asp Tyr Arg Gly Phe Asp Lys Arg
625                 630                 635                 640

Asn Glu Thr Pro Ile Tyr Glu Phe Gly Tyr Gly Leu Ser Tyr Thr Thr
                645                 650                 655

Phe Asn Tyr Ser Asn Leu Glu Val Gln Val Leu Ser Ala Pro Ala Tyr
            660                 665                 670

Glu Pro Ala Ser Gly Glu Thr Glu Ala Ala Pro Thr Phe Gly Glu Val
        675                 680                 685

Gly Asn Ala Ser Asn Tyr Leu Tyr Pro Asp Gly Leu Gln Lys Ile Thr
    690                 695                 700

Lys Phe Ile Tyr Pro Trp Leu Asn Ser Thr Asp Leu Glu Ala Ser Ser
705                 710                 715                 720

Gly Asp Ala Ser Tyr Gly Gln Asp Ser Ser Asp Tyr Leu Pro Glu Gly
                725                 730                 735

Ala Thr Asp Gly Ser Ala Gln Pro Ile Leu Pro Ala Gly Gly Gly Pro
            740                 745                 750

Gly Gly Asn Pro Arg Leu Tyr Asp Glu Leu Ile Arg Val Ser Val Thr
        755                 760                 765

Ile Lys Asn Thr Gly Lys Val Ala Gly Asp Glu Val Pro Gln Leu Tyr
    770                 775                 780

Val Ser Leu Gly Gly Pro Asn Glu Pro Lys Ile Val Leu Arg Gln Phe
785                 790                 795                 800

Glu Arg Ile Thr Leu Gln Pro Ser Glu Thr Lys Trp Ser Thr Thr
                805                 810                 815

Leu Thr Arg Arg Asp Leu Ala Asn Trp Asn Val Glu Lys Gln Asp Trp
            820                 825                 830

Glu Ile Thr Ser Tyr Pro Lys Met Val Phe Val Gly Ser Ser Ser Arg
        835                 840                 845

Lys Leu Pro Leu Arg Ala Ser Leu Pro Thr Val His
    850                 855                 860

<210> SEQ ID NO 7
<211> LENGTH: 2812
<212> TYPE: DNA
<213> ORGANISM: Aspergillus aculeatus

<400> SEQUENCE: 7
ccatggtacc cggatcctcg cttcaacatc tttctcaaat tctcgagagc gcaagctgtg      60
tggctggcta gctcgttgct tcctctttct tcagctacct ctacgccatc atgaagctca     120
gttggcttga ggcggctgcc ttgacggctg cttcagtcgt cagcgctgat gaactggcgt     180
tctctcctcc tttctacccc ctccgtgggg ccaatggcca gggagagtgg gcggaagcct     240
accagcgtgc agtggccatt gtatcccaga tgactctgga tgagaaggtc aacctgacca     300
ccggaactgg atgggagctg agaagtgcg tcggtcagac tggtggtgtc ccaagactga     360
acatcggtgg catgtgtctt caggacagtc ccttgggaat tcgtgatagt gactacaatt     420
cggctttccc tgctggtgtc aacgttgctg cgacatggga caagaacctt gcttatctac     480
gtggtcaggc tatgggtcaa gagttcagtg acaaaggaat tgatgttcaa ttgggaccgg     540

```
ccgcgggtcc cctcggcagg agccctgatg gaggtcgcaa ctgggaaggt ttctctccag    600
acccggctct tactggtgtg ctctttgcgg agacgattaa gggtattcaa gacgctggtg    660
tcgtggcgac agccaagcat tacattctca atgagcaaga gcatttccgc caggtcgcag    720
aggctgcggg ctacggattc aatatctccg acacgatcag ctctaacgtt gatgacaaga    780
ccattcatga aatgtacctc tggcccttcg cggatgccgt tcgcgccggc gttggcgcca    840
tcatgtgttc ctacaaccag atcaacaaca gctacggttg ccagaacagt tacactctga    900
acaagcttct gaaggccgag ctcggcttcc agggctttgt gatgtctgac tggggtgctc    960
accacagtgg tgttggctct gctttggccg gcttggatat gtcaatgcct ggcgatatca   1020
ccttcgattc tgccactagt ttctggggta ccaacctgac cattgctgtg ctcaacggta   1080
ccgtcccgca gtggcgcgtt gacgacatgg ctgtccgtat catggctgcc tactacaagg   1140
ttggccgcga ccgcctgtac cagccgccta acttcagctc ctggactcgc gatgaatacg   1200
gcttcaagta tttctacccc caggaagggc cctatgagaa ggtcaatcac tttgtcaatg   1260
tgcagcgcaa ccacagcgag gttattcgca agttgggagc agacagtact gttctactga   1320
agaacaacaa tgccctgccg ctgaccggaa aggagcgcaa agttgcgatc ctgggtgaag   1380
atgctggatc caactcgtac ggtgccaatg gctgctctga ccgtggctgt gacaacggta   1440
ctcttgctat ggcttggggt agcggcactg ccgaattccc atatctcgtg acccctgagc   1500
aggctattca agccgaggtg ctcaagcata agggcagcgt ctacgccatc acggacaact   1560
gggcgctgag ccaggtggag accctcgcta acaagccagt gtctctctct gtatttgtca   1620
actcggacgc gggagagggc tatatctccg tggacggaaa cgagggcgac cgcaacaacc   1680
tcaccctctg gaagaacggc gacaacctca tcaaggctgc tgcaaacaac tgcaacaaca   1740
ccatcgttgt catccactcc gttggacctg ttttggttga cgagtggtat gaccacccca   1800
acgttactgc catcctctgg gcgggcttgc ctggccagga gtctggcaac tccttggctg   1860
acgtgctcta cggccgcgtc aacccggggcg ccaaatctcc attcacctgg ggcaagacga   1920
gggaggcgta cggggattac cttgtccgtg agctcaacaa cggcaacgga gctccccaag   1980
atgatttctc ggaaggtgtt ttcattgact accgcggatt cgacaagcgc aatgagaccc   2040
cgatctacga gttcggacat ggtctgagct acaccacttt caactactct ggccttcaca   2100
tccaggttct caacgcttcc tccaacgctc aagtagccac tgagactggc gccgctccca   2160
ccttcggaca gtcggcaat gcctctgact acgtgtaccc tgagggattg accagaatca   2220
gcaagttcat ctatccctgg cttaattcca cagacctgaa ggcctcatct ggcgacccgt   2280
actatggagt cgacaccgcg gagcacgtgc ccgagggtgc tactgatggc tctccgcagc   2340
ccgttctgcc tgccggtggt ggctctgtgg gtaacccgcg cctctacgat gagttgatcc   2400
gtgtttcggt gacagtcaag aacactggtc gtgttgccgg tgatgctgtg cctcaattgt   2460
atgtttccct tggtggaccc aatgagccca aggttgtgtt gcgcaaattc gaccgcctca   2520
ccctcaagcc ctccgaggag acggtgtgga cgactaccct gacccgccgc gatctgtcta   2580
actgggacgt tgcggctcag gactgggtca tcacttctta cccgaagaag gtccatgttg   2640
gtagctcttc gcgtcagctg ccccttcacg cggcgctccc gaaggtgcaa tgagcagctg   2700
aaggtgttgt gaaggaaggg ctttgggcct cagcttcagc ttgcagctga agatgatgta   2760 tacattttc ccaagtcgta gagactacga atttaatgac tatgatgctg tc            2812
```

```
<210> SEQ ID NO 8
<211> LENGTH: 38
<212> TYPE: DNA
<213> ORGANISM: Artificial
<220> FEATURE:
<223> OTHER INFORMATION: BGL1-F

<400> SEQUENCE: 8
aactgcaggc ggccgcatca tgaagctcag ttggcttg                             38

<210> SEQ ID NO 9
<211> LENGTH: 27
<212> TYPE: DNA
<213> ORGANISM: Artificial
<220> FEATURE:
<223> OTHER INFORMATION: BGL1-R

<400> SEQUENCE: 9
aagcatgctc attgcacctt cgggagc                                         27

<210> SEQ ID NO 10
<211> LENGTH: 24
<212> TYPE: DNA
<213> ORGANISM: Artificial
<220> FEATURE:
<223> OTHER INFORMATION: FbgI S641T

<400> SEQUENCE: 10
ctttcaacta cactggcctt caca                                            24

<210> SEQ ID NO 11
<211> LENGTH: 27
<212> TYPE: DNA
<213> ORGANISM: Artificial
<220> FEATURE:
<223> OTHER INFORMATION: FbgI R738T

<400> SEQUENCE: 11
ctggtggtaa cgcgaccctc tacgatg                                         27

<210> SEQ ID NO 12
<211> LENGTH: 24
<212> TYPE: DNA
<213> ORGANISM: Artificial
<220> FEATURE:
<223> OTHER INFORMATION: FbgI R745N

<400> SEQUENCE: 12
gatgagttga tcaacgtttc ggtg                                            24

<210> SEQ ID NO 13
<211> LENGTH: 19
<212> TYPE: DNA
<213> ORGANISM: Artificial
<220> FEATURE:
<223> OTHER INFORMATION: Fbgi K787N

<400> SEQUENCE: 13
tcaccctcaa tccctccga                                                  19

<210> SEQ ID NO 14
<211> LENGTH: 23
<212> TYPE: DNA
<213> ORGANISM: Artificial
<220> FEATURE:
<223> OTHER INFORMATION: FbgI E790N
```

```
<400> SEQUENCE: 14
caagccctcc aacgagacgg tgt                                          23

<210> SEQ ID NO 15
<211> LENGTH: 23
<212> TYPE: DNA
<213> ORGANISM: Artificial
<220> FEATURE:
<223> OTHER INFORMATION: Fbgi V793N

<400> SEQUENCE: 15
cgaggagacg aactggacga cta                                          23

<210> SEQ ID NO 16
<211> LENGTH: 23
<212> TYPE: DNA
<213> ORGANISM: Artificial
<220> FEATURE:
<223> OTHER INFORMATION: FbgI T797N

<400> SEQUENCE: 16
gtggacgact aacctgaccc gcc                                          23

<210> SEQ ID NO 17
<211> LENGTH: 23
<212> TYPE: DNA
<213> ORGANISM: Artificial
<220> FEATURE:
<223> OTHER INFORMATION: FbgI D807T

<400> SEQUENCE: 17
gtctaactgg actgttgcgg ctc                                          23

<210> SEQ ID NO 18
<211> LENGTH: 24
<212> TYPE: DNA
<213> ORGANISM: Artificial
<220> FEATURE:
<223> OTHER INFORMATION: Fbgi V814N

<400> SEQUENCE: 18
ctcaggactg gaacatcact tctt                                         24

<210> SEQ ID NO 19
<211> LENGTH: 23
<212> TYPE: DNA
<213> ORGANISM: Artificial
<220> FEATURE:
<223> OTHER INFORMATION: Fbgi S826N

<400> SEQUENCE: 19
ccatgttggt aactcttcgc gtc                                          23
```

MUTANT β-GLUCOSIDASE

FIELD OF THE INVENTION

The present invention relates to a mutant β-glucosidase.

BACKGROUND OF THE INVENTION

A technology is known for producing a saccharide from cellulose in a biomass material containing cellulose (hereinafter, sometimes refers to as "biomass") and converting the saccharide to energies such as ethanol and chemical products using a fermentation method. Efforts made on environmental issues in recent years have helped advancement in various technological development for the industrial use of biomasses, and mass production of fuels and chemical products using biomass has also been realized.

Biomass is composed of cellulose fibers, hemicellulose surrounding the cellulose fibers and containing mainly xylan, and lignin. In the production of saccharide using biomass as a raw material, it is important to increase saccharification efficiency of cellulose and hemicellulose and the achievement thereof requires a biomass saccharification enzyme such as a cellulase and a hemicellulase which hydrolyzes cellulose and hemicellulose. For example, for efficiently degrading cellulose into glucose, at least three types of cellulases need to work in concert with each other, such as (1) a cellobiohydrolase (CBH) which cleaves off a saccharide in a cellobiose unit from the end of crystalline and non-crystalline cellulose fibers, (2) an endoglucanase (EG) which makes a cleavage into the cellulose chain by working on the non-crystalline cellulose, and (3) a β-glucosidase (BGL) which produces glucose by hydrolyzing the cellobiose produced by these enzymes.

Fungi well known to produce a cellulase used for the saccharification of biomass are microorganisms belonging to the genus *Trichoderma* such as *Trichoderma reesei* and *Trichoderma viride*. However, in the biomass saccharification using a cellulase derived from a microorganism belonging to the genus *Trichoderma*, relatively low β-glucosidase activity is noted (Non Patent Literature 1). A technology has been developed for increasing biomass saccharification activity of an enzyme derived from a microorganism belonging to the genus *Trichoderma* by expressing a β-glucosidase of *Aspergillus aculeatus* in the microorganism belonging to the genus *Trichoderma* (for example, Non Patent Literature 1, Patent Literature 1).

During enzymatic degradation of biomass, a biomass saccharification enzyme adsorb on the substrate, cellulose and hemicellulose. Such an adsorption of biomass saccharification enzyme on the biomass substrates is called the productive adsorption. On the other hand, a biomass saccharification enzyme also adsorbs on components which are not degraded by the enzyme, such as lignin, ash, and other components, and this called the nonspecific adsorption. As the primary residual component after biomass is saccharified using a saccharification enzyme is lignin, the nonspecific adsorption of biomass saccharification enzyme on lignin may cause reduction of the enzyme activity. There is a report that the presence of lignin reduced the activity of a β-glucosidase of *Aspergillus niger* (Non Patent Literature 2, Non Patent Literature 3, Non Patent Literature 4).

There is a report on a biomass saccharification enzyme having increased enzyme activity in the presence of lignin. Patent Literature 2 discloses that a cellobiohydrolase (CBH) II derived from a microorganism such as *Thermobifida fusca* had reduced adsorption on non-cellulose materials by modifications such as substitution with negatively charged amino acids and removal of positively charged amino acids. Patent Literature 3 discloses a mutant of *Trichoderma reesei* Family 6 cellulase with reduced inactivation by lignin. Patent Literature 4 discloses a cellulase mutant having increased activity in the presence of lignin and/or inhibited bonding to lignin by modifying a linker peptide. Patent Literature 5 discloses a mutant of carbohydrate-binding module (CBM) of *Trichoderma reesei* Cel6A having increased activity in the presence of lignin and/or inhibited bonding to lignin.

(Patent Literature 1) WO 2013/115305 A1
(Patent Literature 2) JP-A-2011-523854
(Patent Literature 3) WO 2010/012102 A1
(Patent Literature 4) WO 2010/096931 A1
(Patent Literature 5) WO 2011/097713 A1
(Non Patent Literature 1) MORIKAWA Yasushi, Research Frontier of Biomass Degrading Enzymes, 2012, CMC Publishing Co., Ltd., p 10-19
(Non Patent Literature 2) J Biol Chem, 2013, 288 (46): 32991-33005
(Non Patent Literature 3) Analyst, 2009, 134(11):2267-2272
(Non Patent Literature 4) Biotechnol Prog, 2007, 23(2):398-406.

SUMMARY OF INVENTION

The present invention provides a mutant β-glucosidase selected from the group consisting of the following (i) and (ii):

(i) a polypeptide that consists of an amino acid sequence obtained by substituting, with asparagine, at least one amino acid residue at position selected from the group consisting of a position corresponding to position 787, a position corresponding to position 790, and a position corresponding to position 797 of SEQ ID NO: 1, in the amino acid sequence as set forth in SEQ ID NO: 1, or an amino acid sequence having at least 80% identity thereto, and that has β-glucosidase activity; and (ii) a polypeptide that comprises the polypeptide of (i) and has β-glucosidase activity.

Further, the present invention provides a polynucleotide encoding the mutant β-glucosidase.

Further, the present invention provides a vector comprising the polynucleotide.

Further, the present invention provides a transformant comprising the polynucleotide or the vector.

Further, the present invention provides a biomass saccharification agent comprising the mutant β-glucosidase.

Further, the present invention provides a method for producing a saccharide comprising saccharifying biomass using the mutant β-glucosidase.

Further, the present invention provides a method for producing a mutant β-glucosidase, comprising substituting, with asparagine, at least one amino acid residue at position selected from the group consisting of a position corresponding to position 787, a position corresponding to position 790, and a position corresponding to position 797 of SEQ ID NO: 1, in a polypeptide comprising the amino acid sequence as set forth in SEQ ID NO: 1, or an amino acid sequence having at least 80% identity thereto and having β-glucosidase activity.

BRIEF DESCRIPTION OF DRAWINGS

FIG. 1 Relative activity of a mutant β-glucosidase after reaction with saccharification residue. White bar: enzyme concentration 5.6 μg/mL, black bar: enzyme concentration 55.8 μg/mL.

DETAILED DESCRIPTION OF THE INVENTION

In the present Description, the "amino acid residue" means 20 types of amino acid residue constituting a protein such as alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), lysine (Lys or K), methionine (Met or M), phenylalanine (Phe or F), proline (Pro or P), serine (Ser or S), threonine (Thr or T), tryptophan (Trp or W), tyrosine (Tyr or Y), and valine (Val or V).

In the present Description, the identity between amino acid sequences and between nucleotide sequences can be calculated by Lipman-Pearson method (Science, 1985, 227: 1435-41). Specifically, the calculation can be achieved by carrying out an analysis using a homology analysis (Search homology) program of a genetic information processing software Genetyx-Win (Ver. 5.1.1; Software Development) with the Unit size to compare (ktup) being set to 2.

In the present Description, the "at least 80% identity" described pertaining to an amino acid sequence and a nucleotide sequence refers to 80% or more, preferably 85% or more, more preferably 90% or more, further preferably 95% or more, further preferably 98% or more, further preferably 99% or more, further preferably 99.5% or more, further preferably 99.6% or more, further preferably 99.7% or more, and further preferably 99.8% or more identity.

In the present Description, the "one to several" pertaining to the deletion, substitution or addition of an amino acid(s) means preferably from 1 to 160 amino acids, more preferably from 1 to 80 amino acids, further preferably from 1 to 40 amino acids, further preferably from 1 to 20 amino acids, further preferably from 1 to 10 amino acids, and further preferably from 1 to 5 amino acids.

In the present Description, the "position corresponding to" on an amino acid sequence and a nucleotide sequence can be determined by aligning a sequence of interest and a reference sequence (for example, the amino acid sequence as set forth in SEQ ID NO: 1) such that the maximum homology is given to conserved amino acid residues or nucleotides present in each amino acid sequence or nucleotide sequence. The alignment can be carried out using a publicly known algorithm and the procedure therefor is publicly known by those skilled in the art. For example, the alignment can be carried out using a Clustal W multiple alignment program (Nucleic Acids Res, 1994, 22:4673-4680) in default settings. Alternatively, Clustal W2 and Clustal omega, revised versions of Clustal W, can also be used. Clustal N, Clustal W2, and Clustal omega can be used on the websites of, for example, European Bioinformatics Institute (EBI [www.ebi.ac.uk/index.html]) and DNA Data Bank of Japan (DDBJ [www.ddbj.nig.ac.jp/Welcome-j.html]) operated by National Institute of Genetics.

Those skilled in the art can make further fine adjustments on the alignment obtained in the above as needed to achieve the optimum alignment. Such optimum alignment is preferably determined considering the similarity of amino acid sequences and frequency of inserted gaps. The similarity of amino acid sequences herein refers to, when two amino acid sequences are aligned, the percentage (%) of the number of positions at which identical or analogous amino acid residues are present in the two sequences, relative to the number of full-length amino acid residues. Analogous amino acid residues mean, of 20 types of amino acids constituting a protein, amino acid residues having similar properties with each other in the aspect of polarity and electric charge, so called, amino acid residues which cause conservative substitution. The groups consisting of such analogous amino acid residues are well known by those skilled in the art and examples include, but not limited thereto, arginine and lysine; glutamic acid and aspartic acid; serine and threonine; glutamine and asparagine; valine, leucine, and isoleucine, respectively.

The position of amino acid residue or nucleotide on the sequence of interest aligned to position corresponding to any position of the reference sequence by the alignment mentioned above is considered as the "position corresponding to" such any position, and the amino acid residue or nucleotide at the position is referred to as the "amino acid residue at a position corresponding to" or "nucleotide at a position corresponding to".

In the present Description, the "β-glucosidase" (or also referred to as "BGL") refers to a polypeptide having β-glucosidase activity. In the present Description, the "β-glucosidase activity" refers to activity to hydrolyze β-glucosidic bonds of a saccharide, and preferably refers to activity to hydrolyze cellobiose and produce glucose. The β-glucosidase activity of a protein can be determined through the pNP (p-Nitrophenol) method by, for example, measuring an amount of pNP released by enzymatic degradation from 4-nitrophenyl-β-D-glucopyranoside. Specific procedures for measuring the β-glucosidase activity are described in detail in examples to be described later.

In the present Description, the "biomass" refers to cellulosic biomass containing cellulose produced by plants and algae. Specific examples of the biomass include at least one selected from the group consisting of various wood materials obtained from conifers such as Japanese larch and bald cypress and broad-leaf trees such as oil palm (trunk) and Japanese cypress; processed or ground wood materials such as wood chips; pulps such as wood pulp produced from wood materials and cotton linter pulp obtained from fibers around cottonseed; papers such as newspaper, cardboard, magazine, and wood free paper; stem, leaf, and fruit of plants such as bagasse (residue that remains after sugarcane are crushed), palm Empty Fruit Bunch (EFB), rice straw, and cornstalk or leave; plant shells such as chaff, palm shell, and coconut shell; and algae. Of these, wood materials, processed or ground wood materials, and stem, leaf, and fruit of plants are preferable, bagasse, EFB, and oil palm (trunk) are more preferable, and bagasse is further preferable, from a viewpoint of easy availability and raw material cost. These kinds of biomass may be used singly or two or more may be used in mixture. Further, the above biomass may be dried.

In the present Description, the "saccharification residue" refers to a residual solid remained after cellulose and hemicellulose in biomass are saccharified using a saccharification enzyme. Examples of components of the saccharification residue include lignin. The degree of "saccharification residue adsorption" of an enzyme can be calculated by, for example, reacting a saccharification residue with an enzyme to allow the enzyme to adsorb on the saccharification residue, and subsequently measuring activity of the enzyme remained in a supernatant of the reaction solution thereby to determine relative activity to enzyme activity when the enzyme is not reacted with the saccharification residue. For example, saccharification residue adsorbability can be expressed by the following formula.

Saccharification residue adsorbability (%)=100−relative activity (%)

Relative activity (%)=(enzyme activity of enzyme sample after reaction with saccharification residue/enzyme activity of enzyme sample unreacted with saccharification residue)×100

The lower the above relative activity of an enzyme is, the enzyme has higher saccharification residue adsorption. Examples of saccharification residue include, for example, a solid residue remained after alkali-mixed ground bagasse saccharified at 50° C. for 24 hours using a publicly known cellulase or a cellulase formulation (for example, manufactured by Novozymes A/S Cellic (registered trademark) CTec2), or lignin. The reaction of saccharification residue and an enzyme can employ, for example, a treatment at 50° C. for 1 hour. Examples of the specific procedures for measuring the saccharification residue adsorption of an enzyme are described in detail in examples to be described later.

The present invention provides a β-glucosidase mutant capable of more efficiently saccharifying biomass.

The present inventors found a β-glucosidase mutant which has low nonspecific adsorption and can retain high activity in the biomass saccharification reaction.

The mutant β-glucosidase of the present invention has low nonspecific adsorption and can retain high activity in the presence of saccharification residue produced by the biomass saccharification reaction. Thus, the mutant β-glucosidase of the present invention exhibits high β-glucosidase activity in the biomass saccharification reaction. Use of the mutant β-glucosidase of the present invention can improve biomass saccharification efficiency.

The present invention provides a mutant β-glucosidase. The mutant β-glucosidase of the present invention can be produced by modifying a β-glucosidase having the amino acid sequence as set forth in SEQ ID NO: 1, or an amino acid sequence having at least 80% identity thereto, to substitute the amino acid residue(s) at predetermined position(s) with asparagine. The mutant β-glucosidase of the present invention, when compared to such a β-glucosidase before the substitution (parent β-glucosidase), has low saccharification residue (for example, lignin) adsorption (or nonspecific adsorption) thereby less likely reducing enzyme activity in the presence of saccharification residue. Further, the mutant β-glucosidase of the present invention has improved β-glucosidase activity on biomass compared to the parent β-glucosidase.

Thus, in an embodiment, the present invention provides a mutant β-glucosidase containing an amino acid sequence having at least 80% identity to the amino acid sequence as set forth in SEQ ID NO: 1, wherein the amino acid sequence contains asparagine at one or more positions selected from the group consisting of positions corresponding to positions 787, 790, and 797 of SEQ ID NO: 1, and has β-glucosidase activity. Preferably, the amino acid sequence having at least 80% identity to the amino acid sequence as set forth in SEQ ID NO: 1 is an amino acid sequence having 90% or more identity to the amino acid sequence as set forth in SEQ ID NO: 1.

In a preferable embodiment, the mutant β-glucosidase of the present invention is selected from the group consisting of the following (i) and (ii):

(i) a polypeptide that consists of an amino acid sequence obtained by substituting, with asparagine, at least one amino acid residue at a position selected from the group consisting of a position corresponding to position 787, a position corresponding to position 790, and a position corresponding to position 797 of SEQ ID NO: 1 in the amino acid sequence as set forth in SEQ ID NO: 1, or an amino acid sequence having at least 80% identity thereto, and has β-glucosidase activity;

(ii) a polypeptide that contains the polypeptide of (i) and has β-glucosidase activity.

Preferably, the amino acid sequence having at least 80% identity to the amino acid sequence as set forth in SEQ ID NO: 1 is an amino acid sequence having 90% or more identity to the amino acid sequence as set forth in SEQ ID NO: 1.

In another embodiment, the present invention provides a method for producing a mutant β-glucosidase. The method contains substituting, with asparagine, at least one amino acid residue at a position selected from the group consisting of a position corresponding to position 787, a position corresponding to position 790, and a position corresponding to position 797 of SEQ ID NO: 1 in a polypeptide containing the amino acid sequence as set forth in SEQ ID NO: 1, or an amino acid sequence having at least 80% identity thereto and having β-glucosidase activity.

Preferably, the amino acid sequence having at least 80% identity to the amino acid sequence as set forth in SEQ ID NO: 1 is an amino acid sequence having 90% or more identity to the amino acid sequence as set forth in SEQ ID NO: 1.

In the mutant β-glucosidase or production method thereof of the present invention, preferable examples of the amino acid sequence as set forth in SEQ ID NO: 1, or an amino acid sequence having at least 80% identity thereto include any of amino acid sequences as set forth in SEQ ID NOs: 1 to 3; any of amino acid sequences as set forth in SEQ ID NOs: 4 to 6; and an amino acid sequence having deletion, substitution or addition of one to several amino acids with respect to the amino acid sequences as set forth in SEQ ID NOs: 1 to 6 (provided that the amino acid sequence has at least 30%, preferably 90% or more identity to SEQ ID NO: 1).

In the present Description, a β-glucosidase, before the above amino acid substitution, containing the amino acid sequence as set forth in SEQ ID NO: 1, or an amino acid sequence having at least 80% identity thereto (provided that the amino acid residues at positions corresponding to positions 787, 790, and 797 of SEQ ID NO: 1 are not asparagine) is sometimes referred to as the parent β-glucosidase of the mutant glucosidase of the present invention (or simply the parent β-glucosidase or parent BGL).

Examples of the parent BGL include β-glucosidase 1 of *Aspergillus aculeatus* consisting of the amino acid sequence as set forth in SEQ ID NO: 1 (in the present Description, also referred to as AaBGL1, GenBank: BAA10968.1, UniProtKB/Swiss-Prot: P48825.1).

Other examples of the parent BGL include a polypeptide that consists of an amino acid sequence having at least 80% identity to the amino acid sequence as set forth in SEQ ID NO: 1 and has β-glucosidase activity. Examples of such a polypeptide include a BGL derived from the genus *Aspergillus* and consisting of an amino acid sequence having at least 80% identity to the amino acid sequence as set forth in SEQ ID NO: 1, and preferable examples include An18g03570 (SEQ ID NO: 2, GenBank:XP_001398816.1) which is a BGL derived from *Aspergillus niger* (*A. niger*) CBS 513.88 having 82.9% sequence identity to the amino acid sequence as set forth in SEQ ID NO: 1, and BGL (SEQ ID NO: 3, GenBank:BAA19913.1) derived from *Aspergillus kawachii* (*A. kawachii* or *A. awamori* var. *kawachi*) NBRC4308 having 82.5% sequence identity to the amino acid sequence as set forth in SEQ ID NO: 1.

Other examples of the parent BGL include mutants of AaBGL1, An18g03570, and the BGL derived from *Aspergillus kawachii* (SEQ ID NOs: 1 to 3) mentioned above. Examples of such a mutant include a β-glucosidase consisting of an amino acid sequence having deletion, substitution or addition of one to several amino acids with respect to the amino acid sequences as set forth in SEQ ID NOs: 1 to 3 (provided that the amino acid sequence has at least 80% identity, preferably 90% or more identity to SEQ ID NO: 1). Such a mutant may be a naturally occurred mutant or may be artificially created.

Other examples of the parent BGL include a BGL preprotein in which AaBGL1, An18g03570, the BGL derived from *Aspergillus kawachii* (SEQ ID NOs: 1 to 3) mentioned above or a mutant thereof and a secretion signal sequence are bound. Preferable examples of the preprotein include preproteins of AaBGL1, An18g03570, and the BGL derived from *Aspergillus kawachii* with a secretion signal sequence, each consisting of the amino acid sequences as set forth in SEQ ID NOs: 4 to 6. Other examples of the preprotein include a BGL preprotein consisting of an amino acid sequence having deletion, substitution or addition of one to several amino acids with respect to the amino acid sequences as set forth in SEQ ID NOs: 4 to 6 (provided that the amino acid sequence has at least 80% identity, preferably 90% or more identity to SEQ ID NO: 1).

The parent BGLs mentioned above preferably have lysine at a position corresponding to position 787, glutamic acid at a position corresponding to position 790, and threonine at a position corresponding to position 797 of the amino acid sequence as set forth in SEQ ID NO: 1.

The mutant BGL of the present invention can be produced by, for example, expressing a polynucleotide encoding the mutant BGL of the present invention. Preferably, the mutant BGL of the present invention can be produced from a transformant into which a polynucleotide encoding the mutant BGL is introduced. Namely, the mutant BGL of the present invention is produced when a polynucleotide encoding the mutant BGL of the present invention or a vector containing such a polynucleotide is introduced into a host cell to obtain a transformant, and subsequently the transformant is cultured in a suitable medium to express the introduced polynucleotide. The mutant BGL of the present invention can be obtained by isolating or purifying the produced mutant BGL from the culture product.

Thus, the present invention further provides a polynucleotide encoding the mutant BGL of the present invention, and a vector containing such a polynucleotide. The present invention further provides a method for producing a transformant including introducing a polynucleotide encoding the mutant BGL of the present invention or a vector containing such a polynucleotide into a host cell. The present invention further provides a transformant containing such a polynucleotide or vector. The present invention further provides a method for producing a mutant BGL including culturing such a transformant.

The polynucleotide encoding the mutant BGL of the present invention may encompass single strand or double strand DNA, cDNA, RNA, and other artificial nucleic acids. These DNA, cDNA, and RNA may be chemically synthesized. Further, the polynucleotide of the present invention may also contain a nucleotide sequence of an untranslated region (UTR) in addition to open reading frames (ORF).

The polynucleotide encoding the mutant BGL of the present invention can be genetically engineered or chemically synthesized based on the amino acid sequence of the mutant BGL. For example, the polynucleotide encoding the mutant glucosidase of the present invention can be prepared by, in the polynucleotide encoding the parent BGL mentioned above (hereinafter also referred to as the parent BGL gene), mutating a nucleotide sequence (codon) encoding at least one amino acid residue at position selected from the group consisting of positions corresponding to positions 787, 790, and 797 of SEQ ID NO: 1 to a nucleotide sequence (codon) encoding asparagine. Expression of such a mutated polynucleotide enables the obtention of the mutant BGL in which the amino acid residue to be substituted is substituted with asparagine.

Examples of the parent BGL gene include the polynucleotide encoding AaBGL1 as set forth in SEQ ID NO: 1, the polynucleotide encoding An18g03570 as set forth in SEQ ID NO: 2 and the polynucleotide encoding the BGL derived from *Aspergillus kawachii* as set forth in SEQ ID NO: 3, and the polynucleotides encoding the preprotein (SEQ ID NOs: 4 to 6) having a secretion signal sequence thereof as mentioned above. Preferable examples include the polynucleotide (SEQ ID NO: 7) encoding AaBGL1 (SEQ ID NO: 1) or the preprotein thereof (SEQ ID NO: 4). These polynucleotides can be obtained by any method used in the related fields. For example, the polynucleotide encoding the amino acid sequence as set forth in SEQ ID NO: 1 can be obtained by extracting the whole genome DNA of *Aspergillus aculeates*, subsequently selectively amplifying a target nucleic acid by PCR using primers designed based on the sequence of SEQ ID NO: 7, and purifying the amplified nucleic acid.

Alternatively, examples of the parent BGL gene include a polynucleotide encoding the parent BGL mentioned above which consists of an amino acid sequence having at least 80% identity to the amino acid sequence as set forth in SEQ ID NO: 1. Examples of such a polynucleotide include a polynucleotide encoding a mutant of AaBGL1, An18g03570, and the BGL derived from *Aspergillus kawachii* (SEQ ID NOs: 1 to 3) mentioned above. The parent BGL gene may be a naturally occurred gene or may be artificially created based on the sequence of SEQ ID NOs: 1 to 3. For example, a mutation is introduced into a gene encoding the amino acid sequence of SEQ ID NOs: 1 to 3 (for example, SEQ ID NO: 7) by a publicly known mutagenesis method such as ultraviolet irradiation and site directed mutagenesis, and the β-glucosidase activity of the polypeptide encoded by the obtained mutant gene is investigated. Selection of the gene encoding the polypeptide having the desired activity enables the obtention of the parent BGL gene. The gene sequence can be confirmed by sequencing as needed. The procedures of such a mutation are well known by those skilled in the art.

Introduction of a mutation of interest into the parent BGL gene can be carried out using various site directed mutagenesis methods well known by those skilled in the art. The site directed mutagenesis method can be carried out by any technique such as, for example, inverse PCR method and annealing method (by Muramatsu et al. version, "Kaitei Dai4 pan Shin Idenshi Kogaku Handcbukku (in Japanese)" ("Revised 4th Edition, New Gene Engineering Handbook"), Yodosha Co., Ltd., p. 82-88. Various commercially available kits for site directed mutagenesis such as QuickChange II Site-Directed Mutagenesis Kit and QuickChange Multi Site-Directed Mutagenesis Kit by Stratagene Inc can also be used as needed. Alternatively, the site directed mutagenesis into the parent BGL gene can be carried out by publicly known techniques such as SOE (splicing by overlap extension)-PCR method (Horton R. M. et al, Gene, 1989, 77(1):61-68) and megaprimer method.

For example, the site directed mutagenesis into the parent BGL gene can be carried out using mutation primers containing a nucleotide mutation to be introduced. Such mutation primers may be designed such that they anneal to a region containing a nucleotide sequence encoding the amino acid residue to be substituted in the parent BGL gene and contain a nucleotide sequence having a nucleotide sequence (codon) encoding asparagine in place of a nucleotide sequence (codon) encoding the amino acid residue to be substituted. Those skilled in the art can suitably recognize and select the nucleotide sequence (codon) encoding the amino acid residue to be substituted and the amino acid residue substituted based on a typical textbook.

Mutation primers can be prepared by well-known oligonucleotide synthesis method such as phosphoramidite method (Nucleic Acids Research, 1989, 17:7059-7071). Further, mutation primers can also be prepared using, for example, a commercially available oligonucleotide synthesizer (manufactured by ABI). When the site directed mutagenesis as described above is carried out using a primer set containing mutation primers and the parent BGL gene as a template DNA, the polynucleotide encoding a mutant BGL of interest can be obtained.

The vector containing the polynucleotide encoding the mutant BGL of the present invention can be prepared by introducing such a gene into a vector. Type of vector into which such a polynucleotide is introduced is not particularly limited and examples thereof include a vector typically used for the protein production such as a plasmid, cosmid, phage, virus, YAC, and BAC. Of these, a plasmid vector is preferable, and a plasmid vector inducing high expression of a protein is more preferable. Those skilled in the art can select a preferable vector depending on the type of host cell. A plasmid vector for protein expression may be prepared according to a host cell but a commercially available product may also be used. Examples of the vector include a yeast expression vectors pNAN8142 (Biosci Biotechnol Biochem, 1996, 60:383-389) and pMA91 (Biosci Biotechnol Biochem, 1998, 62:1615-1618).

The vector can encompass a DNA fragment containing a DNA replication initiation region or a DNA region containing a replication point. Alternatively, in such a vector, regulatory regions such as a promoter region, a terminator region or a secretion signal region for extracellularly secreting the expressed protein may be operably linked to the above polynucleotide encoding the mutant BGL of the present invention. Alternatively, a marker gene (for example, drug resistance genes such as ampicillin, neomycin, kanamycin, and chloramphenicol) for selecting a host cell into which the vector is suitably introduced may further be incorporated. Alternatively, when an auxotrophic strain is used as a host cell into which the vector of the present invention is introduced, a vector containing a gene encoding a nutrient required may be used.

Preferable examples of the regulatory region include P-No8142 promoter (Biosci Biotechnol Biochem, 1996, 60:383-389) and *Trichoderma reesei*-derived cbh1 promoter sequence (Curr Genet, 1995, 28(1):71-79). Alternatively, a promoter expressing a saccharification enzyme such as a cellobiohydrolase, endoglucanase, β-glucosidase, xylanase, and β xylosidase may be used. Alternatively, a promoter of a metabolic pathway enzyme such as a pyruvate decarboxylase, alcohol dehydrogenase, and pyruvate kinase may be used.

Linkage of the sequence encoding the mutant BGL of the present invention to the above regulatory region or marker gene sequence can be carried out by a method such as SOE-PCR method mentioned above. The procedure of introducing a gene sequence into the vector is well known in the related fields. The type of regulatory regions such as promoter region, terminator and secretion signal region is not particularly limited, and a promoter and secretion signal sequence typically used can be suitably selected and used depending on a host cell into which they are introduced.

The transformant containing the polynucleotide encoding the mutant BGL of the present invention or the vector containing such a polynucleotide can be obtained by introducing the vector into a host cell or introducing the polynucleotide into the genome of a host cell. The method for introducing the vector into a host cell usable can be a method typically used in the related fields such as the protoplast method or the electroporation method. When a strain into which the introduction is suitably made is selected with the marker gene expression and auxotroph as an indicator, the transformant of interest into which the vector is introduced can be obtained.

The method for introducing the polynucleotide encoding the mutant BGL of the present invention into the genome of a host cell is not particularly limited but includes, for example, a double cross system using a DNA fragment containing such a polynucleotide. The DNA fragment may be introduced downstream of the promoter sequence of a gene with a high expression level in the host cell mentioned above, or a fragment in which the DNA fragment is operably linked to the regulatory region mentioned above is prepared in advance and the linked fragment may be introduced into the genome of a host cell. Further, the DNA fragment may be linked in advance to the marker (drug resistant gene and auxotrophic complementary gene) for selecting a cell into which the polynucleotide of the present invention is suitably introduced.

In the present Description, the polynucleotide encoding the BGL and the regulatory region are "operably linked" refers to that the polynucleotide and the regulatory region are arranged in such a way that the BGL encoded by the polynucleotide can be expressed under the regulation of the regulatory region.

Examples of the host cell for such a transformant include a microorganism such as yeast, a filamentous fungus, and a bacterium. Examples of the yeast include *Rhizopus oryzae*, *Saccharomyces cerevisiae*, and *Pichia pastoris*. Examples of the bacterium include *Escherichia coli*, and bacterium belonging to the genus *Staphylococcus*, the genus *Enterococcus*, the genus *Listeria*, and the genus *Bacillus*, and of which, *Escherichia coli* and the bacterium belonging to the genus *Bacillus* (for example, *Bacillus subtilis* or mutant strains hereof) are preferable. Examples of the *Bacillus subtilis* mutant strain include the nine-protease-deficient strain, KA8AX, described in J Biosci Bioeng, 2007, 104(2): 135-143 and the eight-protease-deficient strain having increased protein folding efficiency, D8PA, described in Biotechnol Lett, 2011, 33(9):1847-1852. Examples of the filamentous fungus include the genus *Trichoderma*, the genus *Aspergillus*, and the genus *Rhizopus*, and of which, the genus *Trichoderma* is preferable from a viewpoint of enzyme productivity.

When the thus obtained transformant into which the polynucleotide encoding the mutant BGL of the present invention or the vector containing such a polynucleotide is introduced is cultured in a suitable medium, the polynucleotide is expressed and the mutant BGL of the present invention is produced. The medium used for culturing such a transformant can be suitably selected by those skilled in the art depending on the type of transformant microorganism.

Alternatively, the mutant BGL of the present invention may be expressed from a polynucleotide encoding the mutant BGL of the present invention or a transcript thereof using a cell-free translation system. The "cell-free translation system" is an in vitro transcription-translation system or an in vitro translation system constructed by adding a reagent such as an amino acid required for protein translation to a suspension obtained by mechanically disrupting cells to be the host cell.

The mutant BGL of the present invention produced in the above culture product or the cell-free translation system can be isolated or purified by using a routine method used for protein purification such as centrifugation, ammonium sulfate precipitation, gel chromatography, ion exchange chromatography, and affinity chromatography singly or in a suitable combination. At this time, when the polynucleotide encoding the mutant BGL and the secretion signal sequence are operably linked on the vector in the transformant, the obtained BGL is extracellularly secreted and thus can be easily collected from the culture product. The BGL collected from the culture product may further be purified by a publicly known means.

The mutant β-glucosidase of the present invention, as shown in examples to be described later, has low saccharification residue (for example, lignin) adsorption (or nonspecific adsorption) compared to the β-glucosidase before the mutation (parent BGL) and is less likely to reduce activity in the presence of saccharification residue. Additionally, the mutant β-glucosidase of the present invention has increased β-glucosidase activity on biomass compared to the parent BGL (FIG. 1, Table 2). Thus, the mutant β-glucosidase of the present invention is useful as an enzyme for biomass saccharification.

Thus, the present invention further provides a biomass saccharification agent containing the mutant β-glucosidase of the present invention. The present invention further provides a method for producing a saccharide including saccharifying biomass using the mutant β-glucosidase of the present invention.

The biomass saccharification agent of the present invention is preferably an enzyme composition for biomass saccharification containing the mutant β-glucosidase of the present invention (hereinafter also referred to as the enzyme composition of the present invention). The enzyme composition of the present invention contains the mutant BGL of the present invention, and preferably further contains an additional biomass saccharification enzyme other than the mutant BGL of the present invention from a viewpoint of increasing the saccharification efficiency. The additional biomass saccharification enzyme may be an enzyme derived from an animal, plant, and microorganism. Examples of the additional biomass saccharification enzyme include an additional cellulase other than the mutant BGL of the present invention such as an endoglucanase, exoglucanase, cellobiohydrolase, and BGL other than the mutant BGL of the present invention, and a hemicellulase such as a xylanase, xylosidase, and galactanase, preferably an additional cellulase other than the mutant BGL of the present invention, and more preferably at least one selected from the group consisting of a cellobiohydrolase and endoglucanase. These biomass saccharification enzymes may be used singly or two or more of them may be used in combination. The enzyme composition of the present invention preferably contains, from a viewpoint of increasing the biomass saccharification efficiency, at least one selected from the group consisting of a cellobiohydrolase and endoglucanase.

Specific examples of the additional cellulase other than the mutant BGL of the present invention, which is contained in the enzyme composition of the present invention include, but not limited thereto, a cellulase derived from *Trichoderma reesei*; cellulase derived from *Trichoderma viride*; cellulase derived from various *Bacillus* strains such as *Bacillus* sp. KSM-N145 (FERN P-19727), *Bacillus* sp. KSM-N252 (FERN P-17474), *Bacillus* sp. KSM-N115 (FERN P-19726), *Bacillus* sp. KSM-N440 (FERN P-19728), and *Bacillus* sp. KSM-N659 (FERN P-19730); heat resistant cellulase derived from *Pyrococcus horikoshii*; and cellulase derived from *Humicola insolens*. Of these, a cellulase derived from *Trichoderma reesei*, *Trichoderma viride*, or *Humicola insolens* is preferable from a viewpoint of increasing the saccharification efficiency. Further, a recombinant cellulase obtained by expressing a cellulase gene exogenously introduced into the above microorganism may also be used. Specific examples include cellulase JN11 produced by X3AB1 strain (J Ind Microbiol Biotechnol, 2012, 1741-1749) obtained by introducing a β-glucosidase gene derived from *Aspergillus aculeatus* into *Trichoderma reesei*. Alternatively, a cellulase formulation containing the above additional cellulase may be contained in the enzyme composition of the present invention and used in combination with the mutant BGL of the present invention. Specific examples of the cellulase formulation include Cellcrust (registered trademark) 1.5 L (manufactured by Novozymes A/S), TP-60 (manufactured by Meiji Co., Ltd.), Cell (registered trademark) CTec2 (manufactured by Novozymes A/S), Accellerase™DUET (manufactured by Genencor), and Ultraflo (registered trademark) L (manufactured by Novozymes A/S).

Specific examples of the cellobiohydrolase contained in the enzyme composition of the present invention include a cellobiohydrolase derived from *Trichoderma reesei*, *Trichoderma viride*, or *Humicola insolens*, and heat resistant cellobiohydrolase derived from *Pyrococcus horikoshii*. Of these, a cellobiohydrolase derived from *Trichoderma reesei*, *Trichoderma viride*, or *Humicola insolens* is preferable from a viewpoint of increasing the saccharification efficiency, and a cellobiohydrolase derived from *Trichoderma reesei* is more preferable.

Specific examples of the endoglucanase contained in the enzyme composition of the present invention include an enzyme derived from *Trichoderma reesei*, *Acremonium celluloriticus*, *Humicola insolens*, *Clostridium thermocellum*, *Bacillus*, *Thermobifida*, and *Cellulomonas*. Of these, an endoglucanase derived from *Trichoderma reesei*, *Humicola insolens*, *Bacillus*, or *Cellulomonas* is preferable, and an endoglucanase derived from *Trichoderma reesei* is more preferable from a viewpoint of increasing the saccharification efficiency.

Examples of the additional BGL other than the mutant BGL of the present invention contained in the enzyme composition of the present invention include a BGL derived from *Aspergillus niger* (for example, Novozyme 188 manufactured by Novozymes A/S and BGL manufactured by Megazyme Ltd.) and a BGL derived from *Trichoderma reesei* or *Penicillium emersonii*. Of these, Novozyme 188 and a BGL derived from *Trichoderma reesei* are preferable, and a BGL derived from *Trichoderma reesei* is more preferable from a viewpoint of increasing the biomass saccharification efficiency.

Examples of the hemicellulase contained in the enzyme composition of the present invention include a hemicellulase derived from *Trichoderma reesei*; a xylanase derived from *Bacillus* sp. KSM-N546 (FERM P-19729); a xylanase derived from *Aspergillus niger, Trichoderma viride, Humicola insolens*, or *Bacillus alcalophilus*; a xylanase derived from the genus *Thermomyces, Aureobasidium, Streptomyces, Clostridium, Thermotoga, Thermoascus, Caldocellum*, or *Thermomonospora*; a β-xylosidase derived from *Bacillus pumilus*; and a β-xylosidase derived from *Selenomonas ruminantium*. Of these, a xylanase derived from *Bacillus* sp., *Aspergillus niger, Trichoderma viride* or *Streptomyces* or a β-xylosidase derived from *Selenomonas ruminantium* is preferable, and a xylanase derived from *Bacillus* sp. or *Trichoderma viride* or a β-xylosidase derived from *Selenomonas ruminantium* is more preferable from a viewpoint of increasing the saccharification efficiency. Alternatively, examples of preferable hemicellulase include a mutant xylanase described in JP-A-2013-243953, JP-A-2013-243954, JP-A-2015-167552, JP-A-2016-119877, JP-A-2017-012006, and JP-A-2017-035001.

The content of the mutant BGL of the present invention in the biomass saccharification agent of the present invention (or the enzyme composition of the present invention) is, in the total protein amount, preferably 0.5 mass % or more, more preferably 1 mass % or more, and further preferably 2 mass % or more, and preferably 70 mass % or less, more preferably 50 mass % or less, further preferably 40 mass % or less, and further preferably 30 mass % or less, or, in the total protein amount, preferably from 0.5 to 70 mass %, more preferably from 1 to 50 mass %, further preferably from 2 to 40 mass %, and further preferably from 2 to 30 mass %. Preferably, the total protein amount of the biomass saccharification agent of the present invention (or the enzyme composition of the present invention) is from 3 to 25 mass %.

The content of the additional cellulases other than the mutant BGL of the present invention in the enzyme composition of the present invention is, in the total protein amount thereof, preferably 10 mass % or more, more preferably 30 mass % or more, and further preferably 50 mass % or more, and preferably 99 mass % or less, and more preferably 95 mass % or less, or, in the total protein amount thereof, preferably from 10 to 99 mass %, more preferably from 30 to 95 mass %, and further preferably from 50 to 95 mass %.

The content of endoglucanase in the enzyme composition of the present invention is, in the total protein amount thereof, preferably 1 mass % or more, more preferably 5 mass % or more, and further preferably 10 mass % or more, and preferably 70 mass % or less, more preferably 50 mass % or less, and further preferably 40 mass % or less, or, in the total protein amount thereof, preferably from 1 to 70 mass %, more preferably from 5 to 50 mass %, and further preferably from 10 to 40 mass %.

The content of the hemicellulase in the enzyme composition of the present invention is, in the total protein amount thereof, preferably 0.01 mass % or more, more preferably 0.1 mass % or more, and further preferably 0.5 mass % or more, and preferably 30 mass % or less, and more preferably 20 mass % or less, or, in the total protein amount thereof, preferably from 0.01 to 30 mass %, more preferably from 0.1 to 20 mass %, and further preferably from 0.5 to 20 mass %.

The method for producing a saccharide of the present invention includes saccharifying biomass using the above mutant BGL of the present invention. In the method, the enzyme composition of the present invention mentioned above may be used as the mutant BGL of the present invention. Conditions for the saccharification treatment in the method of the present invention are not particularly limited as long as the conditions do not deactivate the mutant BGL of the present invention and other enzyme(s) used in combination therewith. Suitable conditions can be suitably determined by those skilled in the art based on the type of biomass, procedures of pretreatment step(s), and the type of enzyme(s) to be used.

In the saccharification treatment, it is preferable to add the mutant BGL of the present invention to a suspension containing biomass. The content of biomass in the suspension is, from a viewpoint of increasing the saccharification efficiency or the saccharide production efficiency (namely, saving time for saccharide production), preferably from 0.5 to 20 mass %, more preferably from 3 to 15 mass %, and further preferably from 5 to 10 mass %.

The amount of the mutant BGL of the present invention to be used in the suspension can be suitably determined based on the type, shape, and amount of biomass and the type and properties of enzyme(s) to be used in combination therewith. Preferably, the amount of the mutant BGL to be used in terms of mass based on biomass mass is from 0.04 to 600 mass %, more preferably from 0.1 to 100 mass %, and further preferably from 0.1 to 50 mass %.

Reaction pH of the saccharification treatment is, from a viewpoint of increasing the saccharification efficiency or the saccharide production efficiency and reducing the production cost, preferably from pH 4 to 9, more preferably from pH 5 to 8, and further preferably from pH 5 to 7. Reaction temperature of the saccharification treatment is, from a viewpoint of increasing the saccharification efficiency, increasing the saccharification efficiency or the saccharide production efficiency and reducing the production cost, preferably from 20 to 90° C., more preferably from 25 to 85° C., further preferably from 30 to 80° C., further preferably from 40 to 75° C., further preferably from 45 to 65° C., further preferably from 45 to 60° C., and further preferably from 50 to 60° C. Reaction time of the saccharification treatment can be suitably set in accordance with the type, shape, and amount of biomass and the amount of enzyme(s). Reaction time is, from a viewpoint of increasing the saccharification efficiency or the saccharide production efficiency and reducing the production cost, preferably from 1 to 5 days, more preferably from 1 to 4 days, and further preferably from 1 to 3 days.

Further, the method for producing saccharide of the present invention further preferably includes, from a viewpoint of increasing the biomass saccharification efficiency or the saccharide production efficiency, a step of pretreating the biomass before saccharifying the biomass using the mutant BGL of the present invention. Examples of the pretreatment include one or more selected from the group consisting of alkali treatment, grinding treatment, and hydrothermal treatment. For the pretreatment, alkali treatment is preferable from a viewpoint of increasing the saccharification efficiency, it is preferable to carry out alkali treatment and grinding treatment from a viewpoint of further increasing the saccharification efficiency, and it is more preferable to carry out alkali treatment and grinding treatment simultaneously. The grinding treatment may be wet grinding or dry grinding, but dry grinding is preferable. More preferably, solid alkali and biomass are together subjected to grinding treatment, to carry out dry grinding in tandem with alkali treatment (alkali-mixed grinding treatment).

Hereinafter, the following substances, production methods, purposes of use, and methods are disclosed in the present Description as exemplary embodiments of the present invention. However, the present invention not limited to these embodiments.

[1] A mutant β-glucosidase selected from the group consisting of the following (i) and (ii):

(i) a polypeptide that consists of an amino acid sequence obtained by substituting, with asparagine, at least one amino acid residue at position selected from the group consisting of a position corresponding to position 787, a position corresponding to position 790, and a position corresponding to position 797 of SEQ ID NO: 1, in the amino acid sequence as set forth in SEQ ID NO: 1, or an amino acid sequence having at least 80% identity thereto, and has β-glucosidase activity; and (ii) a polypeptide that comprises the polypeptide of (i) and has β-glucosidase activity.

[2] The mutant β-glucosidase according to [1], wherein preferably the amino acid sequence as set forth in SEQ ID NO: 1, or an amino acid sequence having at least 80% identity thereto is the amino acid sequence as set forth in any of SEQ ID NOs: 1 to 6, or an amino acid sequence having deletion, substitution or addition of one to several amino acids with respect to the amino acid sequence as set forth in any of SEQ ID NOs: 1 to 6.

[3] The mutant β-glucosidase according to [1] or [2], wherein preferably the mutant β-glucosidase has low saccharification residue adsorption compared to a parent β-glucosidase thereof.

[4] The mutant β-glucosidase according to any one of [1] to [3], wherein preferably the mutant β-glucosidase has enhanced β-glucosidase activity on biomass compared to a parent β-glucosidase thereof.

[5] The mutant β-glucosidase according to [3] or [4], wherein preferably the parent β-glucosidase consists of an amino acid sequence having at least 80% identity to the amino acid sequence as set forth in SEQ ID NO: 1 and has lysine at a position corresponding to position 787, glutamic acid at a position corresponding to position 790, and threonine at a position corresponding to position 797 of the amino acid sequence as set forth in SEQ ID NO: 1.

[6] A polynucleotide encoding the mutant β-glucosidase according to any one of [1] to [5].

[7] A vector comprising the polynucleotide of [6].

[8] A transformant comprising the polynucleotide of [6] or the vector of [7].

[9] The transformant according to [8], wherein the transformant is preferably a filamentous fungus.

[10] A biomass saccharification agent comprising the mutant β-glucosidase of any one of [1] to [5].

[11] A method for producing a saccharide, comprising saccharifying biomass using the mutant β-glucosidase of any one of [1] to [5].

[12] A method for producing a mutant β-glucosidase, comprising substituting, with asparagine, at least one amino acid at position selected from the group consisting of a position corresponding to position 787, a position corresponding to position 790, and a position corresponding to position 797 of SEQ ID NO: 1 in a polypeptide comprising the amino acid sequence as set forth in SEQ ID NO: 1, or an amino acid sequence having at least 80% identity thereto and having β-glucosidase activity.

[13] The method according to [12], wherein preferably the polypeptide comprising the amino acid sequence as set forth in SEQ ID NO: 1, or an amino acid sequence having at least 80% identity thereto and having β-glucosidase activity has lysine at a position corresponding to position 787, glutamic acid at a position corresponding to position 790, and threonine at a position corresponding to position 797 of the amino acid sequence as set forth in SEQ ID NO: 1.

[14] The method according to [12] or [13], wherein preferably the mutant β-glucosidase has low saccharification residue adsorption compared to the polypeptide comprising the amino acid sequence as set forth in SEQ ID NO: 1, or an amino acid sequence having at least 80% identity thereto, and having β-glucosidase activity.

[15] The method according to any one of [12] to [14], wherein preferably the mutant β-glucosidase has enhanced β-glucosidase activity on biomass compared to the polypeptide comprising the amino acid sequence as set forth in SEQ ID NO: 1, or an amino acid sequence having at least 80% identity thereto and having β-glucosidase activity.

[16] The method according to any one of [12] to [15], wherein preferably the polypeptide comprising the amino acid sequence as set forth in SEQ ID NO: 1, or an amino acid sequence having at least 80% identity thereto and having β-glucosidase activity consists of the amino acid sequence as set forth in any of SEQ ID NOs: 1 to 6, or an amino acid sequence having deletion, substitution or addition of one to several amino acids with respect to the amino acid sequence as set forth in any of SEQ ID NOs: 1 to 6.

EXAMPLES

Hereinafter, the present invention is described in further detail in reference with examples but technical scopes of the present invention are not limited to these examples.

Example 1

Construction of Mutant BGL Expression Plasmid

Expression plasmids encoding mutants obtained by introducing the following mutations into β-glucosidase 1 (AaBGL1; SEQ ID NO: 1) of *Aspergillus aculeatus* were constructed: S641T, R738T, R745N, K787N, E790N, V793N, T797N, D807T, V814N, and S826N.

Mutation was introduced into a gene (AaBGL1 gene, SEQ ID NO: 7) encoding AaBGL1 preprotein having a secretion signal sequence by the PCR-megaprimer method. Namely, using each mutation primer and BGL1-R primer shown in Table 1 and using *Aspergillus aculeatus* No. F-50 strain genome DNA as a template, the gene downstream from the site at which mutation had been introduced in the AaBGL1 gene were amplified using PrimeSTAR HS DNA Polymerase in accordance with the attached protocol. The amplified fragments were isolated and collected by agarose gel electrophoresis. Using the obtained amplified fragments with BGL1-F primer as a megaprimer, PCR was carried out by the same method using the F-50 strain genome DNA as a template to amplify the full-length AaBGL1 gene into which the mutation was introduced. The obtained DNA fragment was cleaved at the primer-derived Not I and Sph I sites and incorporated to the same sites of a filamentous fungus expression vector pNAN8142 (Biosci Biotechnol Biochem, 1996, 60:383-389) to construct the expression plasmid. Correct introduction of the mutation into the DNA fragment was confirmed by sequencing.

TABLE 1

| Name | Sequence (5' → 3') | SEQ ID: No |
|---|---|---|
| BGL1-F | AACTGCAGGCGGCCGCATCATGAAGCTCAGTTGGCTTG | 8 |
| BGL1-R | AAGCATGCTCATTGCACCTTCGGGAGC | 9 |

(Mutagtion primer)

| Name | Variant | Sequence (5' → 3') | SEQ ID: No |
|---|---|---|---|
| FbgI S641T | S641T | CTTTCAACTACACTGGCCTTCACA | 10 |
| FbgI R738T | R738T | CTGGTGGTAACGCGACCCTCTACGATG | 11 |
| FbgI R745N | R745N | GATGAGTTGATCAACGTTTCGGTG | 12 |
| FbgI K787N | K787N | TCACCCTCAATCCCTCCGA | 13 |
| FbgI E790N | E790N | CAAGCCCTCCAACGAGACGGTGT | 14 |
| FbgI V793N | V793N | CGAGGAGACGAACTGGACGACTA | 15 |
| FbgI T797N | T797N | GTGGACGACTAACCTGACCCGCC | 16 |
| FbgI D807T | D807T | GTCTAACTGGACTGTTGCGGCTC | 17 |
| FbgI V814N | V814N | CTCAGGACTGGAACATCACTTCTT | 18 |
| FbgI S826N | S826N | CCATGTTGGTAACTCTTCGCGTC | 19 |

Example 2

Preparation of Mutant BGL Expression Strain

A transformant was prepared in accordance with the method of Gomi et al. (Agric Biol Chem, 1987, 51:2549-2555). Namely, 5 mL of a Tween/saline solution (0.1% (w/v) Tween (registered trademark) 80, 0.01% NaCl) was added to an *Aspergillus oryzae* (*A. oryzae*) nia D300 strain grown in MM ($NH_4^+$) plate medium (1.0% Glucose, 0.3% Ammonium tartrate, 0.13% KCl, 0.13% $MgSO_4 \cdot 7H_2O$, 0.38% $KH_2PO_4$, 0.00011% $Mo_7O_{24} \cdot 4H_2O$, 0.00011% $H_3BO_3$, 0.00016% $CoCl_2 \cdot 6H_2O$, 0.00016% $CuSO_4 \cdot 5H_2O$, 0.005% EDTA, 0.0005% $FeSO_4 \cdot 7H_2O$, 0.0005% $MnCl_2 \cdot 4H_2O$, 0.0022% $ZnSO_4 \cdot 7H_2O$, pH 6.5) and spores were suspended using a spreader. The spore suspension was added to 2.00 mL of MM ($NH_4^+$) liquid medium (500-mL Erlenmeyer flask with baffles) and cultured with shaking at 30° C. and 160 rpm overnight. The culturing was finished when suitable growth was achieved and cells were collected on Miracloth and washed with Protoplasting buffer (hereinafter, PB; 0.8M NaCl, 10 mM $NaH_2PO_4$). The collected cells were put in a 50-mL centrifuge tube, suspended in 10 rat of PB containing 30 mg of Yatalase (manufactured by TAKARA Bio Inc.) and 50 mg of Lysing enzyme (manufactured by Sigma-Ardrich), and incubated (30° C., 90 min) while gently shaking. Further, the cells were loosened by pipetting every 30 minutes. Thereafter, the suspension was filtered using Miracloth to collect only protoplasts and the obtained filtrate was centrifuged (4° C., 2000 rpm, 5 min). The precipitate was suspended in 10 mL of Transformation buffer I (hereinafter, TB I; 0.8M NaCl, 10 mM Tris-HCl [pH 7.5], 50 mM $CaCl_2$) and centrifuged (4° C., 2000 rpm, 5 min). Thereafter, the supernatant was removed and the precipitate was suspended in 200 μL of TB I to prepare a protoplast solution. The number of protoplasts was confirmed using a microscope and about $10^7$ cells/mL of protoplasts were used for the subsequent operation.

An equivalent amount of 2× TB I was added to a solution containing about 10 μg of the expression plasmid DNA obtained in Example 1 and the obtained solution was added to the protoplast solution. Further, 0.2 times the amount of Transformation buffer II (hereinafter, TB II; 50% PEG6000, 50 mM Tris-HCl [pH 7.5], 50 mM $CaCl_2$) was added thereto, mixed gently, and allowed to stand for 10 min on ice. Thereafter, 1 mL of TB II was added and allowed to stand at room temperature for 15 min. Subsequently, 10 mL of TB I was added and the solution was centrifuged (4° C., 2000 rpm, 5 min). The supernatant was removed and the precipitate was suspended in 200 of TB I, put on Regeneration medium (hereinafter, RE; 1.0% Glucose, 0.3% $NaNO_3$, 4.68% NaCl, 0.13% KCl, 0.13% $MgSO_4 \cdot 7H_2O$, 0.38% $KH_2PO_4$, 0.00011% $Mo_7O_{24} \cdot 4H_2O$, 0.00011% $H_3BO_3$, 0.00016% $CoCl_2 \cdot 6H_2O$, 0.00016% $CuSO_4 \cdot 5H_2O$, 0.005% EDTA, 0.0005% $FeSO_4 \cdot 7H_2O$, 0.0005% $MnCl_2 \cdot 4H_2O$, 0.0022% $ZnSO_4 \cdot 7H_2O$, pH 6.5), and a top agar (RE, 0.7% agar) was layered on. The obtained transformant was monoclonalized to purify the nucleus. Namely, two microtubes to each of which 200 μL of a Tween/saline solution was added were prepared, and spores of the transformant scraped with the tip of a platinum loop from the RE medium plate in which the transformant had grown was suspended in one of the Tween/saline solutions. 2 μL was taken therefrom and mixed with the other Tween/saline solution to dilute 100-fold. 100 μL of the solution was spread on MM ($NO_3^-$, 0.1% Triton X-100) ($NaNO_3$ was added in place of ammonium tartrate of MM($NH_4^+$) and further Triton X-100 was added) plate medium and statically cultured at 30° C. for 3 to 4 days. One strain was selected from the colonies grown therein and isolated in MM($NO_3^-$) plate medium. The obtained transformant was cultured in 5 mL of MM ($NO_3^-$) liquid medium at 30° C. for 4 days.

Example 3

Purification of the Mutant BGL

The mutant BGL enzyme was purified from the mutant BGL expression strain obtained in Example 2, and the BGL activity thereof was measured by the pNP (p-Nitrophenol) method. An enzyme solution was prepared by diluting the culture supernatant. A 1.5 mM pNP-Glc solution (100 mM Na-acetate buffer, pH 5.0) was used as a substrate solution. An equivalent amount of the 1.5 mM substrate solution was mixed with 100 μL of the enzyme solution preincubated at 37° C. for 5 min to start the enzyme reaction. After reaction at 37° C. for 10 min, 2 mL of a 1M $Na_2CO_3$ solution was added to stop the reaction. Then, absorbance at 405 nm was measured to calculate a concentration of released pNP using an extinction coefficient of pNP (ε405 nm=0.0185 mL/nmol $cm^{-1}$), whereby an enzyme activity was determined. For a blank, a solution nonreactive to the enzyme in which 2 mL of 1M $Na_2CO_3$ and 100 μL of the substrate solution were sequentially added to 100 μL of the enzyme solution was used. The amount of enzyme which releases 1 μmol of pNP for 1 minute was defined as 1 Unit, and an enzyme activity of the culture supernatant was calculated from the following formula.

Enzyme activity (Unit/mL)=$A$405/18.5×2.2 mL/(10 min)×(1/0.1 mL)×dilution rate of culture supernatant As a result, the supernatants containing S641T, R738T, R745N, K787N, E790N, V793N, T797N, D807T, V814N, or S826N mutant showed the BGL activity.

Subsequently, mutant BGLs were purified from the culture supernatants in which the BGL activity was confirmed. The purification was carried out by the following procedures in accordance with the method of Baba et al. (AMB Express, 2015, 5:3). A high expression strain of each mutant enzyme was cultured for 3 days in 1,200 mL (200 mL×6) of MM(NO$_3^-$) liquid medium which contains 5% Glc and 1.5% Na$_2$NO$_3$ as a sole carbon source and nitrogen source, followed by collecting cells using a Buchner funnel. After washing with 5 L of ion exchange water, the cells were suspended in 1,200 mL of Releasing buffer (0.02% Sodium azide, 1 mM PMSF, 10 µg/mL Cycloheximide, 20 mM Na-acetate buffer, pH 5.0) and shaken at 30° C. and 160 rpm for 2 days. After shaken, the filtrate was collected using a Buchner funnel and used as a crude enzyme solution. The crude enzyme was adsorbed on DEAR TOYOPEARL 650M equilibrated with 20 mM Na-acetate buffer (pH 5.0), washed with 4 L of 20 mM Na-acetate buffer (pH 5.0), and subsequently eluted with linear gradient of 1 L of a 0-0.3M NaCl solution (20 mM Na-acetate buffer, pH 5.0). The elution fraction showing the main peak at a value of A280 was collected and subjected to SDS-PAGE to confirm the presence of a band at 130 kDa equivalent to AaBGL1. Further, ammonium sulfate was added to the collected fraction to achieve 30% saturation, the fraction was adsorbed on Butyl TOYOPEARL 650 M equilibrated with 30% saturated ammonium sulfate (20 mM Na-acetate buffer, pH 5.0) in advance, and eluted with reverse linear gradient of 1 L of a 30-0% saturated ammonium sulfate solution (20 mM Na-acetate buffer, pH 5.0). The elution fraction showing the main peak at a value of A280 was collected and subjected to SDS-PAGE to confirm the presence of a band at 130 kDa equivalent to AaBGL1.

Example 4

Test of Adsorption on Saccharification Residue

The mutant BGL purified in Example 3 was investigated for the adsorption on saccharification residue. 2 g of alkali treated bagasse and 10 mg of a *Trichoderma reesei* PC-3-7 strain-derived cellulase culture solution (added to achieve 5 mg/g biomass, Bradford method) were dissolved in 40 mL of 50 mM Na-acetate buffer (pH 5.0) containing 0.2 mg/mL sodium azide and reacted at 50° C. for 24 hours. The reaction solution was centrifuged. (10,000 rpm, 4° C., 10 min) and the precipitate was collected. The collected precipitate was suspended in 40 mL of distilled water and washed by centrifugation again. The washed precipitate was suspended in 36 mL of distilled water to prepare saccharification residue of cellulase-saccharified alkali-treated bagasse (about 90% v/v). To 400 µL of this saccharification residue, 50 µL of 20 mM Na-acetate buffer (pH 5.0) and 5.6 or 55.8 µg/mL of wild-type AaBGL1 (WT) or 50 µL of the mutant enzyme were added to carry out the enzyme reaction with shaking at 50° C. for 1 hour at 160 rpm. After reaction, the reaction solution was centrifuged (15,000 rpm, 4° C., 5 min) and the supernatant was collected. Remained BGL activity of the collected supernatant was measured by the same procedures as in Example 3 using the pNP method, and a relative activity (%) when the remained BGL activity of the reaction solution supernatant added with no saccharification residue was 100% was determined.

The results are shown in FIG. 1. Of the investigated mutant BGLs, the K787N, E790N, and T797N mutants had high remained activity compared to wild-type AaBGL1 (WT), and the adsorption on the saccharification residue was reduced.

These K787N, E790N, and T797N mutants were investigated for specific activity. Using the enzyme purified in Example 3, BGL activity thereof was measured by the same procedures as in Example 3 using pNP method, and the specific activity of the enzyme was calculated by the following formula.

Specific activity (Unit/mg)=enzyme activity (Unit/mL)/protein concentration (mg/mL)

All the mutants had enhanced specific activities compared to the wild type (Table 2). Thus, it was suggested that these mutant BGLs, when compared to the wild type enzyme, had low adsorption on saccharification residue and were less likely to reduce the activity in the presence of saccharification residue, thereby to exhibit high β-glucosidase activity in biomass.

TABLE 2

| Enzyme | Specific activity (U/mg) |
| --- | --- |
| WT | 128 |
| K787N | 201 |
| E790N | 194 |
| T797N | 198 |

In the above, the embodiments of the present invention were described but it should be understood that these are not intended to limit the present invention to the specific embodiments described. Various other alterations and modifications within the scope of the present invention are obvious by those skilled in the art. The literatures and patent applications cited herein are incorporated as reference as if they were completely described in the present Description.

The invention claimed is:

1. A mutant β-glucosidase polypeptide selected from the group consisting of the following (i)(a), (i)(b) and (ii):
   (i) a polypeptide, the amino acid sequence of which consists of
      (a) the amino acid sequence of SEQ ID NO: 1, but in which there is an asparagine in at least one position selected from the group consisting of SEQ ID NO: 1 position 787, SEQ ID NO: 1 position 790, and SEQ ID NO: 1 position 797,
      (b) an amino acid sequence having at least 95% identity to SEQ ID NO: 1 and that has asparagine in at least one position selected from the group consisting of a position corresponding to SEQ ID NO: 1 position 787, a position corresponding to SEQ ID NO: 1 position 790, and a position corresponding to SEQ ID NO: 1 position 797, and that has β-glucosidase activity; and
   (ii) a polypeptide, the amino acid sequence of which comprises the polypeptide of (i)(a) or (i)(b) and that has β-glucosidase activity.

2. The mutant β-glucosidase polypeptide of claim 1, wherein one of SEQ ID NO: 1 positions 787, 790 or 797, or one of the positions corresponding thereto, is asparagine.

3. The mutant β-glucosidase polypeptide of claim 1, wherein more than one of SEQ ID NO: 1 positions 787, 790 or 797, or more than one of the positions corresponding thereto, is asparagine.

4. The mutant β-glucosidase polypeptide of claim 1, wherein the amino acid sequence of the mutant β-glucosidase polypeptide:
comprises an amino acid sequence that has at least 95% identity to the amino acid sequence of SEQ ID NO: 1, and that has asparagine in at least one position selected from the group consisting of a position corresponding to SEQ ID NO: 1 position 787, a position corresponding to SEQ ID NO: 1 position 790, and a position corresponding to SEQ ID NO: 1 position 797.

5. A polynucleotide encoding a mutant β-glucosidase polypeptide, wherein the amino acid sequence of the mutant β-glucosidase polypeptide is selected from the group consisting of the following (i)(a), (i)(b) and (ii):
(i) a polypeptide, the amino acid sequence of which consists of
  (a) the amino acid sequence of SEQ ID NO: 1, but in which there is an asparagine in at least one position selected from the group consisting of SEQ ID NO: 1 position 787, position 790, and position 797,
  (b) an amino acid sequence having at least 95% identity to SEQ ID NO: 1 and that has asparagine in at least one position selected from the group consisting of a position corresponding to SEQ ID NO: 1 position 787, a position corresponding to SEQ ID NO: 1 position 790, and a position corresponding to SEQ ID NO: 1 position 797, and that has β-glucosidase activity;
and
(ii) a polypeptide, the amino acid sequence of which comprises the polypeptide of (i)(a) or (i)(b) and that has β-glucosidase activity.

6. A vector comprising the polynucleotide of claim 5.

7. A transformant comprising the polynucleotide of claim 5.

8. The transformant of claim 7, wherein the transformant is a filamentous fungus.

9. A biomass saccharification agent comprising the mutant β-glucosidase polypeptide of claim 1.

10. A method for producing a saccharide, comprising saccharifying biomass using the mutant β-glucosidase polypeptide of claim 1.

11. A method for producing a mutant β-glucosidase polypeptide, the method comprising substituting asparagine for the amino acid at at least one position selected from the group consisting of a position corresponding to SEQ ID NO: 1 position 787, a position corresponding to SEQ ID NO: 1 position 790, and a position corresponding to SEQ ID NO: 1 position 797 in a parent β-glucosidase polypeptide, wherein the parent β-glucosidase polypeptide comprises the amino acid sequence of SEQ ID NO: 1, or comprises an amino acid sequence having at least 80% identity to SEQ ID NO: 1 and has β-glucosidase activity.

12. The method of claim 11, wherein the mutant β-glucosidase polypeptide has a lower saccharification residue adsorption compared to that of its parent polypeptide.

13. The method of claim 11, wherein the mutant β-glucosidase polypeptide has enhanced β-glucosidase activity on biomass compared to that of its parent polypeptide.

14. The method of claim 11, wherein the parent polypeptide has lysine at a position corresponding to SEQ ID NO: 1 position 787, glutamic acid at a position corresponding to SEQ ID NO: 1 position 790, and threonine at a position corresponding to SEQ ID NO: 1 position 797.

15. A transformant comprising the vector of claim 6.

16. A transformant of claim 15, wherein the transformant is a filamentous fungus.

17. The mutant β-glucosidase polypeptide of claim 1, wherein the amino acid sequence of the mutant β-glucosidase polypeptide
comprises the amino acid sequence of SEQ ID NO: 1, but in which there is an asparagine in at least one position selected from the group consisting of SEQ ID NO: 1 position 787, SEQ ID NO: 1 position 790, and SEQ ID NO: 1 position 797.

18. The mutant β-glucosidase polypeptide of claim 1, wherein the mutant β-glucosidase polypeptide is (ii) a polypeptide, the amino acid sequence of which comprises the polypeptide of (i)(a) or (i)(b) and has β-glucosidase activity.

19. The method of claim 10, wherein the mutant β-glucosidase polypeptide is that of (i)(a): a polypeptide, the amino acid sequence of which is the amino acid sequence of SEQ ID NO: 1, but in which there is an asparagine in at least one amino acid at a position selected from the group consisting of SEQ ID NO: 1 position 787, SEQ ID NO: 1 position 790, and SEQ ID NO: 1 position 797.

20. The method of claim 10, wherein the mutant β-glucosidase polypeptide is (ii) a polypeptide, the amino acid sequence of which comprises the polypeptide of (i)(a) or (i)(b) and has β-glucosidase activity.

21. The mutant β-glucosidase polypeptide of claim 4, wherein the amino acid sequence of the mutant β-glucosidase polypeptide consists of an amino acid sequence that has at least 95% identity to the amino acid sequence of SEQ ID NO: 1, and has asparagine in at least one position selected from the group consisting of a position corresponding to SEQ ID NO: 1 position 787, a position corresponding to SEQ ID NO: 1 position 790, and a position corresponding to SEQ ID NO: 1 position 797.

22. The mutant β-glucosidase polypeptide of claim 17, wherein the amino acid sequence of the mutant β-glucosidase polypeptide consists of the amino acid sequence of SEQ ID NO: 1, but in which there is an asparagine in at least one amino acid at a position selected from the group consisting of SEQ ID NO: 1 position 787, SEQ ID NO: 1 position 790, and SEQ ID NO: 1 position 797.

23. The mutant β-glucosidase polypeptide of claim 1, wherein polypeptide (i)(b) has at least 98% identity with the amino acid sequence of SEQ ID NO: 1.

24. The mutant β-glucosidase polypeptide of claim 21, wherein polypeptide (i)(b) has at least 99.5% identity with the amino acid sequence of SEQ ID NO: 1.

* * * * *